(12) United States Patent
Hosomi

(10) Patent No.: US 8,455,192 B2
(45) Date of Patent: *Jun. 4, 2013

(54) PROBES FOR DETECTION OF SULT1A1 GENE, REAGENT CONTAINING THE SAME, AND THE USES THEREOF

(75) Inventor: Toshiya Hosomi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/086,979

(22) Filed: Apr. 14, 2011

(65) Prior Publication Data

US 2011/0294120 A1 Dec. 1, 2011

Related U.S. Application Data

(62) Division of application No. 12/302,111, filed as application No. PCT/JP2007/073208 on Nov. 30, 2007.

(30) Foreign Application Priority Data

Nov. 30, 2006 (JP) .................................. 2006-322958
Sep. 7, 2007 (JP) .................................. 2007-232615

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 536/23.1; 536/24.3; 435/91.2

(58) Field of Classification Search
None
See application file for complete search history.

(56) References Cited

U.S. PATENT DOCUMENTS

| | | | |
|---|---|---|---|
| 4,889,818 A | 12/1989 | Gelfand et al. | |
| 5,079,352 A | 1/1992 | Gelfand et al. | |

FOREIGN PATENT DOCUMENTS

| | | |
|---|---|---|
| EP | 0455430 A2 | 11/1991 |
| JP | 2005-58107 A | 3/2005 |
| JP | 2005-261354 A | 9/2005 |
| JP | 2006-521092 A | 9/2006 |
| WO | 91/09950 A1 | 7/1991 |
| WO | 92/09689 A1 | 6/1992 |
| WO | 2004/087950 A2 | 10/2004 |

OTHER PUBLICATIONS

Nagai, F. et al., Cytogenet. Cell Genet., vol. 84, pp. 145-147 (1999).*
Rebbeck, T.R. et al., J. Natl. Cancer Inst., vol. 98, pp. 1311-1320 (2006).*
Carlini, E.J. et al., Pharmacogenetics, vol. 11, pp. 57-68 (2001).*
Bernard et al., Integrated amplification and detection of the C677T point mutation in the methylenetetrahydrofolate reductase gene by fluorescence resonance energy transfer and probe melting curves, Anal. Biochem., 255(1):101-107 (1998).
Buck et al., Design strategies and performance of custom DNA sequencing primers, Biotechniques, 27(3):528-536 (1999).
Coughtrie et al., Phenol sulphotransferase SULT1A1 polymorphism: molecular diagnosis and allele frequencies in Caucasian and African populations, Biochem. J., 337:45-49 (1999).
Lilla et al., SULT1A1 genotype, active and passive smoking, and breast cancer risk by age 50 years in a German case-control study, Breast Cancer Res., 7:R229-R237 (2005).
Nowell et al., Relationship of phenol sulfotransferase activity (SULT1A1) genotype to sulfotransferase phenotype in platelet cytosol, Pharmacogenetics, 10(9):789-797 (2005).
Ozawa et al., Genetic pholymorphisms in human liver phenol sulfotransferases involved in the bioactivation of N-hydroxy derivatives of carcinogenic arylamines and heterocyclic amines, Chem. Biol. Interact., 109(1-3):237-248, Abstract (1998).
Raftogianis et al., Phenol sulfotransferase pharmacogenetics in humans: association of common SULT1A1 alleles with TS PST phenotype, Biochem. Biophys. Res. Commun., 239:298-304 (1997).
Raftogianis et al., Human phenol sulfotransferases SULT1A2 and SULT1A1: genetic polymorphisms, allozyme properties, and human liver genotype-phenotype correlations, Biochem. Pharmacol., 58(4):605-616 (1999).
Shatalova et al., Genetic polymorphisms in human SULT1A1 and UGT1A1 genes associate with breast tumor characteristics: a case-series study, Breast Cancer Res., 7(6):R909-921 (2005).
Langsenlehner et al., "Genetic variants of the sulfotransferase 1A1 and breast cancer risk," Breast Cancer Research and Treatment, 87: 19-22 (2004).
Yang et al., "Modifying effects of sulfotransferase 1A1 gene polymorphism on the association of breast cancer risk with body mass index or endogenous steroid hormones," Breast Cancer Research and Treatment, 94: 63-70 (2005).
Office Action issued in corresponding Chinese Patent Application No. 201110063691.6 dated Apr. 6, 2012.
Extended European Search Report issued in corresponding European Patent Application No. 07832873.9 dated Jun. 20, 2012.

* cited by examiner

*Primary Examiner* — Teresa E Strzelecka
(74) *Attorney, Agent, or Firm* — Morgan, Lewis & Bockius LLP

(57) ABSTRACT

A primer set for amplifying a region including sites to be detected of SULT1A1*2 and SULT1A1*3 in the SULT1A1 gene by a gene amplification method is provided, wherein the primer set can amplify the region specifically. A pair of primer set is used including a forward primer consisting of the base sequence of SEQ ID NO: 7 as well as a reverse primer consisting of the base sequence of SEQ ID NO: 18. The use of this primer set makes it possible to specifically and efficiently amplify a region including both sites where two types of polymorphisms (SULT1A1*2 and SULT1A1*3) of the SULT1A1 gene are generated.

10 Claims, 4 Drawing Sheets

PROBES FOR DETECTION OF SULT1A1 GENE, REAGENT CONTAINING THE SAME, AND THE USES THEREOF

RELATED APPLICATIONS

This application is a Divisional Application of U.S. application Ser. No. 12/302,111, filed Nov. 24, 2008, which is a U.S. National Phase Application of International Application No. PCT/JP2007/073208, filed Nov. 30, 2007, which claims the benefit of Japanese Patent Application No. 2006-322958, filed Nov. 30, 2006 and Japanese Patent Application No. 2007-232615, filed Sep. 7, 2007, all of which are herein incorporated by reference in their entireties.

TECHNICAL FIELD

The present invention relates to primer sets for amplifying the SULT1A1 gene, reagents for amplifying the SULT1A1 gene containing the same, and the uses thereof.

BACKGROUND ART

Human tissue sulfotransferase (SULT) plays a role for excreting metabolite of lipophilic substrate, to which hydrogen group was introduced by hepatic cytochrome P450 etc., by metamorphosing it into O-sulfate to improve water solubility thereof. SULT is an enzyme group which is classified into a super family and includes gene families such as SULT 1 and SULT 2. It has been reported that, with respect to an enzyme catalyzing sulfoconjugation reaction of phenol substrate that belongs to a SULT 1 family (PSULT), difference occurs in activation thereof according to gene polymorphisms. Further, since this SULT molecular species catalyzes metabolic activation reaction of cancer-causing allylamine, analysis of gene polymorphism is considered to be very important in terms of disease susceptibility. Specifically, among PSULTs, with respect to a molecular species having p-nitrophenol as a representative substrate in human tissue such as liver and platelets (ST1A3), difference in activation occurs according to a polymorphism of the SULT1A1 gene coding for ST1A3. Further, it is known that the character of activation is associated with colon cancer, migraine liability, etc. Among polymorphisms of the SULT1A1 gene, SULT1A1*2 and SULT1A1*3 are strongly associated with disease susceptibility described above. Therefore, analysis of polymorphisms. SULT1A1*2 and SULT1A1*3, with respect to the SULT1A1 gene is very important for predicting disease susceptibility of patients and for preventing and treating them. SULT1A1*2 is a mutation in which arginine (Arg) at position 213 of amino acid is changed to histidine (His) and SULT1A1*3 is a mutation in which methionine (Met) at position 223 of amino acid is changed to valine (Val).

On the other hand, detection of a point mutation, a so-called single nucleotide polymorphism (SNP), is employed widely as a method of analyzing, at the gene level, for example, the causes of all types of diseases and the individual differences in disease liability (susceptibility to diseases) and in drug action. Examples of the common methods of detecting a point mutation include: (1) a direct sequencing method in which the region corresponding to a sequence to be detected in a target DNA of a sample is amplified by a polymerase chain reaction (PCR) and all the gene sequences are analyzed, (2) a RFLP analysis in which the region corresponding to a sequence to be detected in a target DNA of a sample is amplified by PCR, the amplification product thus obtained is cut with a restriction enzyme whose cleaving action differs depending on the presence or absence of the target mutation in the sequence to be detected and is then electrophoresed, and thereby typing is performed, and (3) the ASP-PCR method in which PCR is performed using a primer with a target mutation located at the 3'-end region and the mutation is judged depending on the presence or absence of amplification.

However, since these methods require, for example, purification of DNA extracted from a sample, electrophoresis, and a treatment with a restriction enzyme, they take time and cost. Furthermore, after PCR is performed, it is necessary to open the reaction container once. Accordingly, there is a possibility that the amplification product may contaminate the next reaction system and thereby the analysis accuracy may be deteriorated. Moreover, since it is difficult to automate, multiple samples cannot be analyzed. Further, the aforementioned ASP-PCR method (3) is less specific, which also is a problem.

Because of these problems, recently, a method of analyzing the melting temperature (Tm) of double-stranded nucleic acid formed of a probe and target nucleic acid is used as a method of detecting a point mutation. Since such a method is performed through, for example, Tm analysis or analysis of the melting curve of the double strand, it is referred to as melting curve analysis. This method is described below. That is, first, a probe complementary to a sequence to be detected containing a target point mutation is used to form a hybrid (double-stranded DNA) between the aforementioned probe and a target single-stranded DNA contained in a detection sample. Subsequently, this hybridization product is heat-treated, and dissociation (melting) of the hybrid accompanying the temperature rise is detected by a change in a signal such as absorbance. The Tm value is then determined based on the result of the detection and the presence or absence of any point mutation is judged accordingly. The higher the homology of the hybridization product, the higher the Tm value, and the lower the homology the lower the Tm value. Therefore the Tm value (reference value for assessment) is determined beforehand with respect to the hybridization product between the sequence to be detected containing a point mutation and a probe complementary thereto, and then the Tm value (measured value) of the hybridization product between the target single-stranded DNA contained in the detection sample and the aforementioned probe is measured. When the measured value is comparable to the reference value, it is considered as matching, that is, it can be judged that a point mutation is present in the target DNA. On the other hand, when the measured value is lower than the reference value, it is considered as mismatching, that is, it can be judged that no point mutation is present in the target DNA. Furthermore, according to this method, it also is possible to automate gene analysis.

However, such a detection method using Tm analysis also has a problem in that a region including a site to be detected must be able to be amplified specifically and efficiently in PCR. Particularly, many isozymes are present in SULT and the sequences for coding them also are very similar to one another. Accordingly, there is a possibility that genes coding for isozymes other than SULT1A1 also are amplified in PCR. Furthermore, when other isozyme-coding genes also have been amplified as described above, it may cause a decrease in reliability of the analysis result in the analysis of, for example, a particular polymorphism (SULT1A1*2 or SULT1A1*3) of the SULT1A1 gene (Nonpatent Document 1 or 2). Moreover, as described above, since analysis of one sample is accompanied by a considerable amount of time and energy it is not practical to analyze multiple samples, which also is a problem.

[Nonpatent Document 1] PMID: 9854023 Biochem J. 1999 Jan. 1; 337 (Pt 1)45-9.

[Nonpatent Document 2] PMID: 9566748 Chem Biol Interact. 1998 Feb. 20; 109 (1-3): 237-48.

DISCLOSURE OF INVENTION

Hence, the present invention is intended to provide primer sets for specifically and efficiently amplifying a target region in the SULT1A1 gene by a gene amplification method.

In order to achieve the aforementioned object, a primer set of the present invention is a primer set for amplifying the SULT1A1 gene by a gene amplification method, wherein the primer set includes the following primer set (1):

Primer Set (1):

a primer set of a pair of primers including a forward primer composed of the following oligonucleotide (F1) and a reverse primer composed of the following oligonucleotide (R1):

(F1): at least one oligonucleotide having a sequence identical to that of a region extending from cytosine (C) at base 3418 to be considered as the first base to any one of the $24^{th}$ to $33^{rd}$ bases in the direction toward the 5' end in the base sequence of SEQ ID NO: 1, with the cytosine (C) being the 3' end, and (R1): at least one oligonucleotide selected from:

at least one oligonucleotide complementary to a region extending from cytosine (C) at base 3607 to be considered as the first base to any one of the $20^{th}$ to $29^{th}$ bases in the direction toward the 3' end in the base sequence of SEQ ID NO: 1, with guanine (G) complementary to the cytosine (C) at base 3607 being the 3' end, and at least one oligonucleotide complementary to a region extending from adenine (A) at base 3576 to be considered as the first base to any one of the $24^{th}$ to $33^{rd}$ bases in the direction toward the 3' end in the base sequence of SEQ ID NO: 1, with thymine (T) complementary to the adenine (A) at base 3576 being the 3' end.

A reagent for amplifying a gene of the present invention is a reagent for amplifying the SULT1A1 gene by a gene amplification method, wherein the reagent includes the primer set for amplifying the SULT1A1 gene of the present invention.

A method of manufacturing an amplification product of the present invention is a method of manufacturing an amplification product of the SULT1A1 gene by a gene amplification method, wherein the method includes the following step (I):

(I) amplifying the SULT1A1 gene in a reaction solution using a primer set for amplifying the SULT1A1 gene according to the present invention, with nucleic acid contained in a sample being used as a template.

A polymorphism analysis method of the present invention is a method of analyzing a polymorphism of a site to be detected in the SULT1A1 gene, wherein the method includes the following steps (i) to (iv):

(i) amplifying a region including a site to be detected in the SULT1A1 gene in a reaction solution by a method of manufacturing an amplification product of the present invention, (ii) preparing a reaction solution that contains the amplification product obtained in step (i) and a probe capable of hybridizing to the site to be detected, (iii) measuring signal values that indicate melting states of a hybridization product between the amplification product and the probe while changing the temperature of the reaction solution, and (iv) determining a polymorphism of the site to be detected from a change in the signal values accompanying a change in the temperature.

The primer set of the present invention makes it possible to specifically and efficiently amplify a region in a reaction solution, with the region including both sites where polymorphisms to be detected (SULT1A1*2 and SULT1A1*3) are respectively generated in the SULT1A1 gene. Accordingly, the time and cost can be reduced, which is different from the conventional methods described above. Furthermore, as described above, since a region including the both sites to be detected of SULT1A1*2 and SULT1A1*3 can be amplified, for example, further the use of a probe complementary to a sequence to be detected including at least one site to be detected described above makes it possible to perform Tm analysis by directly using the aforementioned reaction solution to respectively type the polymorphisms. Moreover, since amplification and typing of a target region including two sites to be detected can be performed with one reaction solution, it is also possible to automate the operation. Since the use of the primer set of the present invention allows a pretreatment to be omitted even in the case of, for example, a contaminated sample (for instance, whole blood or oral mucosa), the amplification reaction can be carried out quicker and more simply. Furthermore, since the use of the primer set of the present invention allows the amplification reaction to be carried out with higher amplification efficiency as compared to the conventional case, the amplification reaction time also can be shortened. Thus, according to the primer set of the present invention and a reagent including the same as well as the method of manufacturing an amplification product and a polymorphism analysis method, in each of which the primer set and the reagent are used, two polymorphisms in the SULT1A1 gene can be analyzed quickly and simply, and it therefore can be said that they are very effective in the field of medicine.

BEST MODE FOR CARRYING OUT THE INVENTION

Primer Set for Amplifying SULT1A1 Gene

Figure 1:
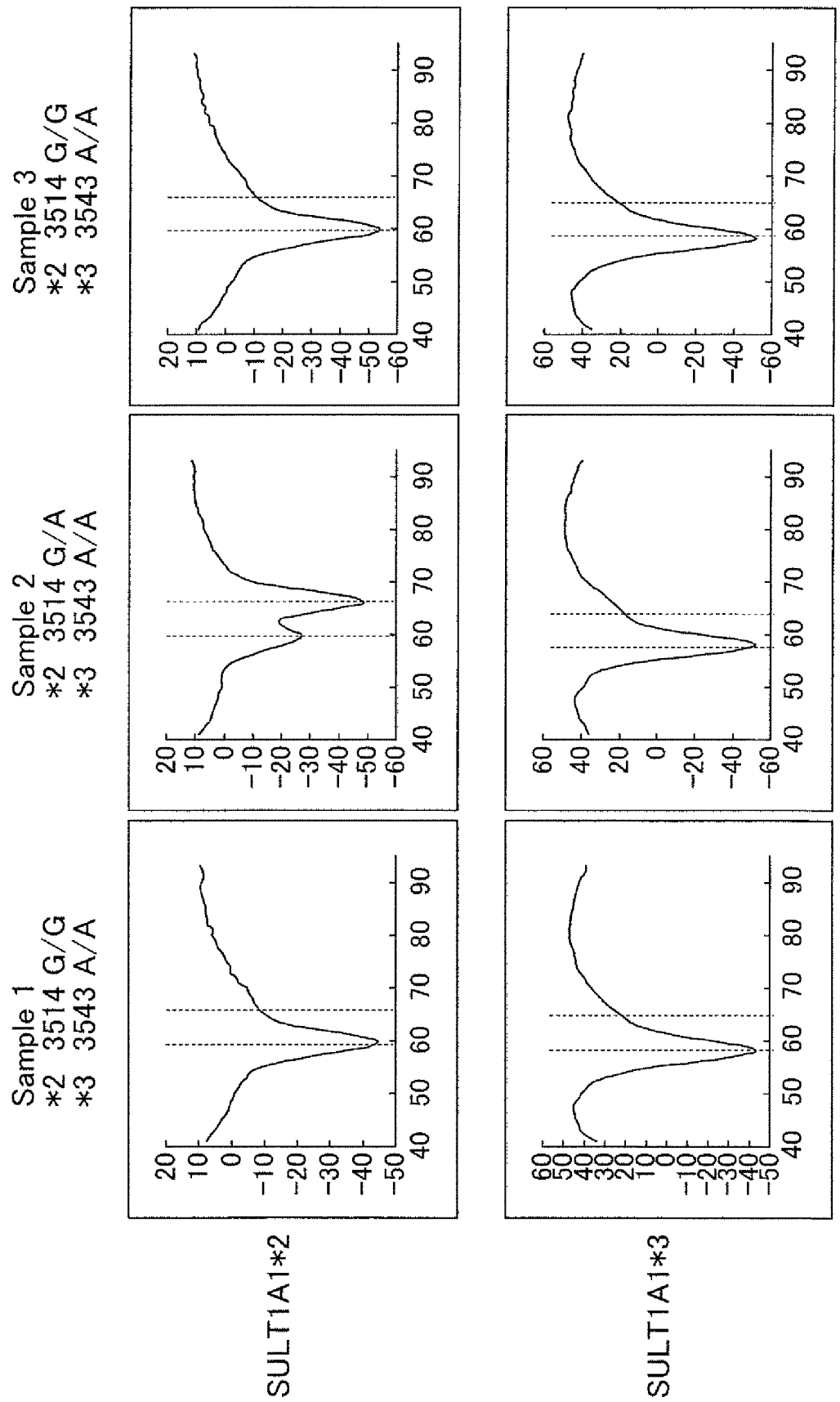
FIG. 1 shows graphs indicating the results of Tm analysis in Example 1 of the present invention.

As described above, the primer set for amplifying the SULT1A1 gene of the present invention is characterized by including the aforementioned primer set (1). Use of this primer set (1) makes it possible, as described above, to specifically amplify a target region including both of a site to be detected where polymorphism SULT1A1*2 is generated and a site to be detected where polymorphism SULT1A1*3 is generated in one reaction solution. Therefore, when this target region is amplified using the primer set of the present invention, polymorphism in the SULT1A1 gene can be analyzed more efficiently as compared to the conventional cases. Hereinafter, a forward primer also may be referred to as "F primer" and a reverse primer as "R primer".

As described above, the primer set (1) is a primer set of a pair of primers including a forward primer composed of the following oligonucleotide (F1) and a reverse primer composed of the following oligonucleotide (R1):

(F1): at least one oligonucleotide having a sequence identical to that of a region extending from cytosine (C) at base 3418 to be considered as the first base to any one of the 24$^{th}$ to 33$^{rd}$ bases in the direction toward the 5' end in the base sequence of SEQ ID NO: 1, with the cytosine (C) being the 3' end, and (R1): at least one oligonucleotide selected from:

at least one oligonucleotide complementary to a region extending from cytosine (C) at base 3607 to be considered as the first base to any one of the 20$^{th}$ to 29$^{th}$ bases in the direction toward the 3' end in the base sequence of SEQ ID NO: 1, with guanine (G) complementary to the cytosine (C) at base 3607 being the 3' end, and at least one oligonucleotide complementary to a region extending from adenine (A) at base 3576 to be considered as the first base to any one of the 24$^{th}$ to 33$^{rd}$ bases in the direction toward the 3' end in the base sequence of SEQ ID NO: 1, with thymine (T) complementary to the adenine (A) at base 3576 being the 3' end.

The base sequence indicated in SEQ ID NO: 1 is a full-length DNA sequence of human sulfotransferase 1 (phenol-preferring phenol sulfotransferase 1; STP1) and, for example, has been registered at NCBI under the accession No. U71086. SEQ ID NO: 1 indicates a sequence of polymorphism having A at base 3514 and G at base 3543.

The primer set (1) is a primer set for amplifying a DNA strand including a region from base 3419 to base 3606 or a region from base 3419 to base 3575 in SEQ ID NO: 1, as well as a strand complementary thereto. Base 3514 in this region (i.e. base 3514 in SEQ ID NO: 1) and base 3543 (i.e. base 3543 in SEQ ID NO: 1) are known for the presence of a point mutation (3514G or 3514A and 3543G or 3543A) that affects the function of SULT1A1. The polymorphism of the former is SULT1A1*2 described above and when the SULT1A1 gene is translated to protein, a polymorphism, in which position 213 of amino acid being arginine (Arg), is indicated in the case where base 3514 is G, and a polymorphism, in which position 213 of amino acid being histidine (His), is indicated in the case where base 3514 is A. In the present invention, the polymorphism of this site can be indicated as 3514G/G or 3514A/A in the case of homozygote and as 3514G/A in the case of heterozygote. Further, polymorphism of the latter is SULT1A1*3 described above and when the SULT1A1 gene is translated to protein, a polymorphism, in which position 223 of amino acid being methionine (Met), is indicated in the case where base 3543 is A, and a polymorphism, in which position 223 of amino acid being valine (Val), is indicated in the case where base 3543 is G. In the present invention, the polymorphism of this site can be indicated as 3543G/G or 3543A/A in the case of homozygote and as 3543G/A in the case of heterozygote. Hereinafter, this primer set (1) also may be referred to as a primer set for SULT1A1".

In the present invention, the F1 primer and R1 primer of the primer set (1) can be any primers, as long as the base located at the 3' end that serves to determine the site from which DNA polymerase starts amplification satisfies the aforementioned condition. Fixation of the base located at the 3' end of each primer in this manner makes it possible to sufficiently prevent the primer set (1) from being bound to, for example, another similar isozyme gene (for example, SULT1A2 gene, SULT1A3 gene, or SULT1A4 gene).

As described above, since the F1 primer and R1 primer each can be any primer as long as the base located at the 3' end is fixed, the length itself of each primer is not particularly limited and can be adjusted suitably to be common length. The length of the primers is, for example, in the range of 13- to 50-mers, preferably 14- to 45-mers, and more preferably 15- to 40-mers. Specifically, it is preferable that the F1 primer be at least one oligonucleotide having a sequence identical to that of a region extending from cytosine (C) at base 3418 to be considered as the first base to any one of the 24$^{th}$ to 33$^{rd}$ bases (preferably the 25$^{th}$ to 32$^{nd}$ bases and more preferably the 26$^{th}$ to 31$^{st}$ bases) in the direction toward the 5' end in the base sequence of SEQ ID NO: 1. Furthermore, it is preferable that the R1 primer be: at least one oligonucleotide complementary to a region extending from cytosine (C) at base 3607 to be considered as the first base to any one of the 20$^{th}$ to 29$^{th}$ bases (preferably the 21$^{st}$ to 26$^{th}$ bases and more preferably the 22$^{nd}$ to 25$^{th}$ bases) in the direction toward the 3' end in the base sequence of SEQ ID NO: 1, or at least one oligonucleotide complementary to a region extending from adenine (A) at base 3576 to be considered as the first base to any one of the 24$^{th}$ to 33$^{rd}$ bases (preferably the 25$^{th}$ to 30$^{th}$ bases and more preferably the 26$^{th}$ to 28$^{th}$ bases) in the direction toward the 3' end in the base sequence of SEQ ID NO: 1. Since each 3' end of the F1 primer and the R1 primer is fixed, the region to be elongated from the primer is, for example, a region from base 3419 to base 3606 or a region from base 3419 to base 3575 in SEQ ID NO: 1 as described above. However, the length of the whole amplification product obtained varies according to the length of the primer to be used.

Furthermore, it is not necessary for the R1 primer and the F1 primer to be oligonucleotides perfectly complementary to the base sequence indicated in SEQ ID NO: 1 and to the strand complementary to the base sequence, respectively. In other words, the part excluding the base located at the 3' end in each primer may be different in one to five bases from that of a perfectly complementary oligonucleotide.

Specific examples of the F1 primer and the R1 primer are indicated below but the present invention is not limited thereto. The combination of these F1 primer and R1 primer is not limited by any means. Specifically, however, a primer set (1') is particularly preferable, which includes a F1' primer composed of oligonucleotide of SEQ ID NO: 7, and a R1' primer composed of oligonucleotide of SEQ ID NO: 18 or SEQ ID NO: 39. "Tm (° C.)" indicated below in the table is Tm (° C.) obtained when each sequence indicated below in the table was hybridized with the sequence perfectly complementary thereto. The "Tm (° C.)" is a value calculated by using MELTCALC software (http://www.meltcalc.com/), with parameters including an oligonucleotide concentration of 0.2 μM and a sodium equivalent (Na eq.) of 50 mM. The Tm value can be calculated by using, for example, conventionally known MELTCALC software (http://www.meltcalc.com/) or also can be determined by the nearest neighbor method (the same applies below).

TABLE 1

| Primer | Sequence | Tm (° C.) | SEQ ID NO. |
|---|---|---|---|
| F Primer | 5'-gcctctgaggttagagaaggggaccccttttac-3' | 65 | 2 |
| | 5'-cctctgaggttagagaaggggaccccttttac-3' | 63.4 | 3 |

TABLE 1-continued

| Primer | Sequence | Tm(° C.) | SEQ ID NO. |
|---|---|---|---|
| | 5'-ctctgaggttagagaaggggaccccttttac-3' | 62.1 | 4 |
| | 5'-tctgaggttagagaaggggaccccttttac-3' | 61.7 | 5 |
| | 5'-ctgaggttagagaaggggaccccttttac-3' | 60.9 | 6 |
| | 5'-tgaggttagagaaggggaccccttttac-3' | 60.5 | 7 |
| | 5'-gaggttagagaaggggaccccttttac-3' | 59.4 | 8 |
| | 5'-aggttagagaaggggaccccttttac-3' | 58.8 | 9 |
| | 5'-ggttagagaaggggaccccttttac-3' | 57.8 | 10 |
| | 5'-gttagagaaggggaccccttttac-3' | 55.9 | 11 |
| R Primer | 5'-ggagatgctgtggtccatgaactcctggg-3' | 65 | 12 |
| | 5'-gagatgctgtggtccatgaactcctggg-3' | 63.7 | 13 |
| | 5'-agatgctgtggtccatgaactcctggg-3' | 63.3 | 14 |
| | 5'-gatgctgtggtccatgaactcctggg-3' | 62.5 | 15 |
| | 5'-atgctgtggtccatgaactcctggg-3' | 62 | 16 |
| | 5'-tgctgtggtccatgaactcctggg-3' | 62.1 | 17 |
| | 5'-gctgtggtccatgaactcctggg-3' | 60.9 | 18 |
| | 5'-ctgtggtccatgaactcctggg-3' | 58.4 | 19 |
| | 5'-tgtggtccatgaactcctggg-3' | 57.6 | 20 |
| | 5'-gtggtccatgaactcctggg-3' | 56.1 | 21 |
| | 5'-ggggacggtggtgtagttggtcatagggttctt-3' | 66.5 | 33 |
| | 5'-gggacggtggtgtagttggtcatagggttctt-3' | 65.3 | 34 |
| | 5'-ggacggtggtgtagttggtcatagggttctt-3' | 64 | 35 |
| | 5'-gacggtggtgtagttggtcatagggttctt-3' | 62.7 | 36 |
| | 5'-acggtggtgtagttggtcatagggttctt-3' | 62.3 | 37 |
| | 5'-cggtggtgtagttggtcatagggttctt-3' | 61.4 | 38 |
| | 5'-ggtggtgtagttggtcatagggttctt-3' | 59.6 | 39 |
| | 5'-gtggtgtagttggtcatagggttctt-3' | 57.9 | 40 |
| | 5'-tggtgtagttggtcatagggttctt-3' | 56.9 | 41 |
| | 5'-ggtgtagttggtcatagggttctt-3' | 55.6 | 42 |

Furthermore, each primer of the aforementioned primer set (1) may be, for example, one with the 5' end to which any conventionally known sequence has been added in order to increase the amplification reaction temperature.

Preferably, a primer set for amplifying the SULT1A1 gene of the present invention including such a primer set (1) is used, for example, in amplifying the SULT1A1 gene in a biological sample such as a whole blood sample. Particularly, when the primer not for amplifying the SULT1A1 gene of the present invention is used in combination with a probe for detecting a polymorphism as described later, it is preferable that the ratio of the whole blood sample to be added to the reaction solution for amplifying a gene be 0.1 to 0.5 vol %. This will be described later.

<Reagent for Amplifying SULT1A1 Gene>

As described above, a reagent for amplifying the SULT1A1 gene of the present invention is a reagent for amplifying the SULT1A1 gene by a gene amplification method, wherein the reagent includes a primer set for amplifying the SULT1A1 gene of the present invention. The reagent for amplifying the SULT1A1 gene of the present invention is characterized by including a primer set of the present invention and, for example, compositions of other than this are not limited by any means.

For example, in order to detect an amplification product obtained by a gene amplification method in which a primer set of the present invention is used, the reagent for amplifying the SULT1A1 gene of the present invention further may include a probe that can hybridize to a site to be detected in the SULT1A1 gene. As described above, the primer set of the present invention can amplify a target region including both sites to be detected of SULT1A1*2 and SULT1A1*3 by a gene amplification method. Accordingly, when a probe complementary to a sequence to be detected including a site to be detected in each target region described above is allowed to coexist, for example, the presence or absence of amplification or the genotype (polymorphism) of the site to be detected can be detected by the method described later. Such probes and the method of using them are explained later in the description of the polymorphism analysis method. Furthermore, it is preferable that the reagent for amplifying the SULT1A1 gene of the present invention be used in amplifying the SULT1A1 gene in a biological sample such as whole blood, for example. Particularly, when the reagent for amplifying the SULT1A1 gene of the present invention is used in combination with the probe described above, it is preferable that the ratio of the whole blood sample to be added to the reaction solution for amplifying a gene be 0.1 to 0.5 vol %. In the present invention, the term "sequence to be detected" denotes a sequence including a site (site to be detected) at which a polymorphism is generated.

The form of the reagent for amplifying the SULT1A1 gene of the present invention is not particularly limited and it may be, for example, a liquid reagent containing a primer set for amplifying the SULT1A1 gene of the present invention or a dry reagent that is to be suspended in a solvent before use. Furthermore, the content of the primer set for amplifying the SULT1A1 gene also is not particularly limited.

<Method of Manufacturing Amplification Product>

As described above, the method of manufacturing an amplification product of the present invention is a method of manufacturing an amplification product of the SULT1A1 gene by a gene amplification method, wherein the method includes the following step (I):

(I) amplifying the SULT1A1 gene in a reaction solution using a primer set for amplifying the SULT1A1 gene of the present invention, with nucleic acid contained in a sample being used as a template.

When a primer set of the present invention is used to perform an amplification reaction in this manner, the target region including both sites to be detected where polymorphisms, SULT1A1*2 and SULT1A1*3, in the SULT1A1 gene are generated can specifically and efficiently be amplified as described above. The method of manufacturing an amplification product of the present invention is characterized in that a primer set of the present invention is used, and, for example, the type of and conditions for the gene amplification method are not limited by any means.

The gene amplification method is not particularly limited as described above. Examples thereof include the polymerase chain reaction (PCR) method, a nucleic acid sequence based amplification (NASBA) method, a transcription-mediated amplification (TMA) method, and a strand displacement amplification (SDA) method. Particularly, the PCR method is preferable. The present invention is described below using the PCR method as an example but is not limited thereby.

The sample to which the present invention is to be applied is not particularly limited as long as it contains, for example, nucleic acid to serve as a template. However, it is preferable that the present invention be applied to, for example, a contaminated sample. Examples of the contaminated sample include whole blood, cells in the mouth (for example, oral mucosa), somatic cells of nails and hairs, germ cells, expectoration, amniotic fluid, paraffin-embedded tissue, urine, gastric juice (for example, gastric lavage fluid), and suspensions thereof. According to the method of manufacturing an amplification product using a primer set of the present invention, for example, even in the case of a sample (particularly, a biological sample such as whole blood or cells in the mouth) with various contaminants such as whole blood, the method is less subject to the effect thereof and allows the target region in the SULT1A1 gene to be amplified specifically. Thus, according to the present invention, even a highly contaminated sample such as whole blood, which is difficult to use in the conventional methods, can be used as it is, for instance, without being pretreated, for example, without being purified. Therefore, it can be said that an amplification product can be prepared quicker as compared to the conventional method also from the viewpoint of the pretreatment of the sample.

The ratio of the sample to be added to the reaction solution is not particularly limited. Specifically, when the sample is a biological sample (for example, a whole blood sample), the lower limit of the ratio thereof to be added to the reaction solution is, for example, preferably at least 0.01 vol %, more preferably at least 0.05 vol %, and further preferably at least 0.1 vol %. Furthermore, the upper limit of the ratio thereof to be added also is not particularly limited and is, for example, preferably 2 vol % or lower, more preferably 1 vol % or lower, and further preferably 0.5 vol % or lower.

When an optical detection to be described later is intended to be performed, particularly, when an optical detection is performed using a labeled probe, it is preferable that the ratio of a biological sample, such as a whole blood sample, to be added be set at, for example, 0.1 to 0.5 vol %. Generally, in the PCR reaction, a heat treatment is carried out to denature DNA (i.e. to dissociate it into a single-stranded DNA). This heat treatment may denature, for example, sugar or protein contained in the sample and thereby may generate an insolubilized precipitate or turbidity. Therefore, when the presence or absence of an amplification product or the genotype (polymorphism) of a site to be detected is to be checked by an optical method, the generation of such a precipitate or turbidity may affect measurement accuracy. However, when the ratio of the whole blood sample to be added to the reaction solution is set in the range described above, for example, an effect caused by generation of, for example, a precipitate due to denaturation can be prevented sufficiently and thereby the accuracy of measurement carried out by the optical method can be improved, although the mechanism thereof is unknown. Furthermore, since it also can sufficiently prevent PCR from being inhibited due to the contaminants contained in a whole blood sample, the amplification efficiency can be improved further. Accordingly, when in addition to the use of a primer set of the present invention, the ratio of the sample such as a whole blood sample to be added is set in the aforementioned range, further the need to pretreat the sample can be omitted.

Furthermore, the ratio of the whole blood sample in the reaction solution can be indicated not in the aforementioned volume ratio (for example, 0.1 to 0.5 vol %) but in a weight ratio of hemoglobin (hereinafter referred to as "Hb"). In this case, the ratio of the whole blood sample in the reaction solution is, for example, preferably in the range of 0.565 to 113 g/L, more preferably in the range of 2.825 to 56.5 g/L, and further preferably in the range of 5.65 to 28.25 µg/L, in terms of the amount of Hb. The ratio of the whole blood sample to be added to the reaction solution may satisfy, for example, both the volume ratio and the Hb weight ratio, or one of them.

The whole blood may be any one of, for example, hemolyzed whole blood, unhemolyzed whole blood, anticoagulated whole blood, and whole blood containing coagulated fractions.

In the present invention, the target nucleic acid contained in a sample is, for example, DNA. The aforementioned DNA may be DNA contained originally in the sample, such as a biological sample, or an amplification product DNA obtained through amplification by a gene amplification method. In the latter case, an example thereof is cDNA that is generated from RNA (for example, total RNA or mRNA) contained originally in the sample by a reverse transcription reaction (for instance, reverse transcription PCR (RT-PCR)).

In the method of manufacturing an amplification product of the present invention, it is preferable that albumin further be added to the reaction solution before the start of a gene amplification reaction. Such addition of albumin further can reduce, for example, the effect of generation of a precipitate or turbidity described above and also further can improve the amplification efficiency. Specifically it is preferable that albumin be added before the amplification reaction in step (I) or a step of dissociation into a single-stranded DNA.

The ratio of albumin to be added to the reaction solution is, for example, in the range of 0.01 to 2 wt %, preferably 0.1 to 1 wt %, and more preferably 0.2 to 0.8 wt %. The albumin is not particularly limited. Examples thereof include bovine serum albumin (BSA), human serum albumin, rat serum albumin, and horse serum albumin. One of them may be used or two or more of them may be used in combination.

Next, a method of manufacturing an amplification product of the present invention is described using an example in which with respect to a whole blood sample including DNA as target nucleic acid, an amplification product of the aforementioned target region of the SULT1A1 gene is produced by PCR using the primer set for amplifying the SULT1A1 gene of the present invention. The present invention is characterized by using primer sets of the present invention and other configurations and conditions are not limited by any means.

First, a PCR reaction solution is prepared. The ratio of the primer sets of the present invention to be added is not particularly limited. However, it is preferable that F primer of the primer set (1) be added to be 0.1 to 2 µmol/L, more preferably 0.25 to 1.5 µmol/L, and particularly preferably 0.5 to 1 µmol/L. Furthermore, it is preferable that R primer of the primer set (1) be added to be 0.1 to 2 µmol/L, more preferably 0.25 to 1.5 µmol/L, and particularly preferably 0.5 to 1 µmol/L. The ratio (F:R, molar ratio) between the F primer and the R primer to be added to the primer set is not particularly limited. It is, for example, preferably 1:0.25 to 1:4 and more preferably 1:0.5 to 1:2.

The ratio of the whole blood sample in the reaction solution is not particularly limited but is preferably in the range described above. The whole blood sample may be added to the reaction solution without being treated or may be added to the reaction solution after being diluted with a solvent such as water or a buffer solution beforehand. When the whole blood sample is diluted beforehand, the dilution ratio is not particularly limited. It can be set so that, for example, the final ratio of the whole blood added to the reaction solution is in the aforementioned range, for example, 1:100 to 1:2000 and preferably 1:200 to 1:1000.

Other composition components in the reaction solution are not particularly limited and can be conventionally known components, whose ratios also are not particularly limited. Examples of the composition components include DNA polymerase, nucleotide (nucleoside triphosphate (dNTP)), and a solvent. Furthermore, as described above, it is preferable that the reaction solution further contain albumin. In the reaction solution, the order of addition of the respective composition components is not limited by any means.

The DNA polymerase is not particularly limited and, for example, a conventionally known thermoduric bacteria-derived polymerase can be used. Specifically, for example, *Thermus aquaticus*-derived DNA polymerase (U.S. Pat. No. 4,889,818 and U.S. Pat. No. 5,079,352) (trade name: Taq polymerase), *Thermus thermophilus*-derived DNA polymerase (WO 91/09950) (rTth DNA polymerase), *Pyroroccus furiosus*-derived DNA polymerase (WO 92/9688) (Pfu DNA polymerase; manufactured by Stratagenes), and *Thermococcus litoralis*-derived DNA polymerase (EP-A 455 430) (Trademark: Vent: manufactured by Biolab New England) are commercially available. Particularly *Thermus aquaticus*-derived thermostable DNA polymerase is preferable.

The ratio of DNA polymerase to be added to the reaction solution is not particularly limited and is, for example, 1 to 100 preferably 5 to 50 U/mL, and more preferably 20 to 30 U/mL. With respect to the unit of activity (U) of DNA polymerase, generally, 1 U denotes the activity that allows all 10 nmol of nucleotide to be taken into an acid-insoluble precipitate in 30 minutes at 74° C. in a reaction solution for activity measurement, with an activated salmon sperm DNA being used as a template primer. The composition of the reaction solution for activity measurement is, for example, 25 mM TAPS buffer (pH 9.3, 25° C.), 50 mM KCl, 2 mM $MgCl_2$, 1 mM mercaptoethanol, 200 μM dATP, 200 μM dGTP, 200 μM dTTP, 100 μM [α-$^{32}$P] dCTP, and 0.25 mg/mL activated salmon sperm DNA.

Generally, examples of the nucleoside triphosphate include dNTP (dATP, dCTP, dTTP). The ratio of dNTP to be added to the reaction solution is not particularly limited and is, for example, 0.01 to 1 mmol/L, preferably 0.05 to 0.5 mmol/L, and more preferably 0.1 to 0.3 mmol/L.

Examples of the solvent include buffer solutions such as Tris-HCl, Tricine, MES, MOPS, HEPES, and CAPS. Commercially available PCR buffer solutions or buffer solutions of commercially available PCR kits can be used.

Furthermore, the PCR reaction solution further may contain heparin betaine, KCl, $MgCl_2$, $MgSO_4$, glycerol, etc. The ratios thereof to be added can be set in ranges in which the PCR reaction is not inhibited.

The total volume of the reaction solution is not particularly limited and can be determined suitably according to, for example, the equipment (thermal cycler) to be used. It is generally 1 to 500 μL and preferably 10 to 100 μL.

Subsequently, PCR is performed. The cycle conditions in PCR are not particularly limited, and, for example, (1) dissociation of whole blood-derived double-stranded DNA into single-stranded DNA, (2) annealing of a primer, and (3) elongation of a primer (polymerase reaction) are as described below. Furthermore, the number of cycles also is not particularly limited but preferably is at least 30, with the following three steps (1) to (3) being considered as one cycle. The upper limit thereof, in total, is not particularly limited and, for example, 100 cycles or less, preferably 70 cycles or less, and further preferably 50 cycles or less. The change in temperature in each step can be controlled automatically using, for example, a thermal cycler. When primer sets of the present invention are used, since they are excellent in amplification efficiency as described above, 50 cycles can be completed in approximately one hour (preferably within one hour) according to the present invention, while it takes approximately three hours to complete 50 cycles according to the conventional methods.

TABLE 2

| | Temperature (° C.) and Time (sec) |
|---|---|
| (1) Dissociation of single-stranded DNA | For example, 90 to 99° C., 1 to 120 sec<br>Preferably, 92 to 95° C., 1 to 60 sec |
| (2) Annealing of primer | For example, 40 to 70° C., 1 to 300 sec<br>Preferably, 50 to 70° C., 5 to 60 sec |
| (3) Elongation reaction | For example, 50 to 80° C., 1 to 300 sec<br>Preferably, 50 to 75° C., 5 to 60 sec |

In the manner described above, amplification products complementary to the region including both the sites to be detected of SULT1A1*2 and SULT1A1*3 in the SULT1A1 gene can be produced.

The method of manufacturing an amplification product of the present invention further may include a step of detecting an amplification product of a target region obtained by the aforementioned amplification reaction. This makes it possible to detect the presence or absence of the amplification product or the genotype (polymorphism, SULT1A1*2 or SULT1A1*3) in the SULT1A1 gene. The presence or absence of the amplification product can be checked by a conventionally known method. Specifically, it can be checked by for example, further adding a probe (for instance, a fluorescently-labeled probe) that can hybridize to one of the sites to be detected in the SULT1A1 gene to the reaction solution in step (I), and further in step (II), measuring the fluorescence intensity of the fluorescent label in the probe with respect to the reaction solution. Alternatively, it can be checked by adding two types of probes (for instance, fluorescently-labeled probes) that can hybridize to two sites to be detected, respectively, and further in step (II), measuring the fluorescence intensity of each fluorescent label in each probe with respect to the reaction solution. Detection of polymorphisms, SULT1A1*2 and SULT1A1*3, in the SULT1A1 gene is described below as an embodiment of the present invention.

<SULT1A1 Gene Polymorphism Analysis Method>

A polymorphism analysis method of the present invention is a method of analyzing the polymorphism of two sites to be detected in the SULT1A1 gene, wherein the method includes the following steps (i) to (iv):

(i) amplifying a region including a site to be detected in the SULT1A1 gene in a reaction solution by a method of manufacturing an amplification product according to the present invention, (ii) preparing a reaction solution that contains the amplification product obtained in step (i) and a probe capable of hybridizing to the site to be detected, (iii) measuring signal values that indicate melting states of a hybridization product between the amplification product and the probe while changing the temperature of the reaction solution, and (iv) determining a polymorphism of the site to be detected from a change in the signal values accompanying a change in the temperature.

In this manner, when an amplification product is produced using a primer set of the present invention, it is possible to amplify the region including both bases to be detected of polymorphisms, SULT1A1*2 and SULT1A1*3, in the SULT1A1 gene as described above, and to analyze each polymorphism in the target region.

The probe to be used in step (ii) is not particularly limited. Examples thereof include a probe that hybridize to a site where a polymorphism SULT1A1*2 is generated (hereinafter, also referred to as a "probe for SULT1A1*2"), and a probe that hybridize to a site where a polymorphism SULT1A1*3 is generated (hereinafter, also referred to as a "probe for SULT1A1*3"). Preferably, these probes are probes complementary to a sequence to be detected containing the aforementioned sequence to be detected. One of the probes may be used or all of the two probes may be used. When all of the two probes are used, for example, polymorphisms in the aforementioned all of two sites to be detected can be analyzed using the same reaction solution.

The probes for detecting the polymorphism are not particularly limited and can be configured by a conventionally known method. For instance, they each may be designed as a sequence to be detected containing a site to be detected of a polymorphism, based on the sequence of a sense strand or the sequence of an antisense strand of the SULT1A1 gene. Furthermore, the base located at the site to be detected of a polymorphism can be determined suitably according to each type of polymorphism. In other words, in the case of SULT1A1*2, since the polymorphism of "G" and "A" at base 3514 in SEQ ID NO: 1 have been known, examples of the probe include a probe complementary to either a sequence to be detected including G at base 3514 or a sequence to be detected including A at base 3514 (a probe for detecting a sense strand), and a probe complementary to a sequence of an antisense strand thereof (a probe for detecting an antisense strand). Further, in the case of SULT1A1*3, since the polymorphism of "G" and "A" at base 3543 in SEQ ID NO: 1 have been known, examples of the probe include a probe complementary to either a sequence to be detected including G at base 3543 or a sequence to be detected including A at base 3543 (a probe for detecting a sense strand), and a probe complementary to a sequence of an antisense strand thereof (a probe for detecting an antisense strand). As described above, when a probe is designed, with the base located at the site to be detected where a polymorphism is generated being set to be any one of the bases as described above, it is also possible to judge what type of polymorphism is expressed at each site to be detected in a SULT1A1 gene by the method as described later.

The probe can be added to an amplified reaction solution after step (i) i.e. after a target region in the SULT1A1 gene is subjected to an amplification reaction. However, it is preferable that the probe be added to a reaction solution before the amplification reaction in step (i) since this allows analysis to be performed easily and quickly.

The ratio of the probe to be added to the reaction solution is not particularly limited. For example, each probe is added to be preferably in the range of 10 to 400 nmol and more preferably in the range of 20 to 400 nmol. When a fluorescent dye is used as the label for a probe, an unlabeled probe with a sequence identical to that of the labeled probe may be used in combination with the labeled probe, for example, in order to adjust the fluorescence intensity to be detected, and the unlabeled probe may include phosphate group added to the 3' end thereof. In this case, the molar ratio between the labeled probe and the unlabeled probe is preferably, for example, 1:10 to 10:1. The length of the probe is not particularly limited. It is, for example, 5- to 50-mers and preferably 10- to 30-mers.

The Tm value is described. When a solution containing double-stranded DNA is heated, the absorbance at 260 nm increases. This is because heating releases the hydrogen bonds between both strands in the double-stranded DNA to dissociate it into single-stranded DNA (i.e. DNA melting). When all double-stranded DNAs are dissociated into single-stranded DNAs, the absorbance thereof indicates approximately 1.5 times that obtained at the start of heating (i.e. absorbance of only double-stranded DNAs), which makes it possible to judge that melting is completed thereby. Based on this phenomenon, the melting temperature Tm generally is defined as a temperature at which the absorbance has reached 50% of the total increase in absorbance.

In the aforementioned step the measurement of the signal values that indicate the melting states of the hybridization product between the amplification product and the probe may be a measurement of absorbance at 260 nm as described above but may be a measurement of the signal of a labeling substance. Specifically, it is preferable that a labeled probe labeled with a labeling substance be used as the aforementioned probe to perform the measurement of the signal of the labeling substance. The labeled probe can be, for example, a labeled probe that exhibits a signal independently but does not exhibit a signal after hybridization, or a labeled probe that does not exhibit a signal independently but exhibits a signal after hybridization. The former probe does not exhibit a signal after forming a hybrid (double-stranded DNA) with a sequence to be detected but exhibits a signal when the probe is released by heating. On the other hand, the latter probe exhibits a signal after forming a hybrid (double-stranded DNA) with a sequence to be detected but the signal is reduced (quenched) when the probe is released by heating. Accordingly, when the signal exhibited by the label is detected under a condition (absorption wavelength etc.) specific to the signal, the progress of melting of the hybridization product and the Tm value can be determined as in the case of the measurement of absorbance at 260 nm.

In the present invention, as described above, the target region amplified includes the sites to be detected that indicate polymorphisms of both SULT1A1*2 and SULT1A1*3. Therefore, use of two types of probes that can respectively hybridize to each site to be detected makes it possible to analyze both polymorphisms. In this case, when the two types of probes are used, it is preferable that they be labeled with different labels each of which is detected under its own condition. The use of different labels as described above makes it possible to analyze each amplification product separately by changing the detection conditions even in the same reaction solution.

Specific examples of labeling substances in the labeled probes include a fluorescent dye (fluorophore). A specific example of the labeled probes is preferably a probe that, for example, has been labeled with a fluorescent dye, exhibits fluorescence independently, and allows fluorescence to be reduced (for example, quenched) after hybridization. Generally, a probe that utilizes such a fluorescence quenching phenomenon is referred to as a fluorescence quenching probe.

Particularly, with respect to the aforementioned probe, it is preferable that the 3' end or 5' end of oligonucleotide be labeled with a fluorescent dye and the base located at the end to be labeled be C. In this case, in the sequence to be detected, to which the labeled probe hybridizes, it is preferable that the base sequence of the labeled probe be designed so that the base to be paired with the end base C of the labeled probe or the base located 1 to 3 bases apart from the base to be paired be G. Generally, such a probe is referred to as a guanine quenching probe and is known as so-called QProbe (registered trademark). When such a guanine quenching probe hybridizes to a sequence to be detected, C located at the end, which has been labeled with a fluorescent dye, approaches G in the DNA to be detected, and thereby a phenomenon occurs that the emission of the fluorescent dye decreases (the fluorescence intensity decreases). The use of such a probe makes it possible to verify hybridization and dissociation easily according to a change in the signal.

The fluorescent dye is not particularly limited. Examples thereof include fluorescein, phosphor, rhodamine, and polymethine dye derivative. Examples of commercially available fluorescent dye include BODIPY FL (brand name, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.). The combination of fluorescent dyes to be used for two types of probes is not particularly limited as long as, for example, it allows the respective probes to be detected under different conditions. Examples thereof include a combination of Pacific Blue (with a detection wavelength of 450 to 480 nm), TAMRA (with a detection wavelength of 585 to 700 nm), and BODIPY FL (with a detection wavelength of 515 to 555 nm).

Specific examples of the sequences of probes for detecting the polymorphisms, SULT1A1*2 and SULT1A1*3, are indicated below, but the present invention is not limited thereto. The following probe (1) is an example of the probe for SULT1A1*2 and is a probe for detecting an antisense strand. The following probe (2) is an example of the probe for SULT1A1*3 and is a probe for detecting an antisense strand.

Probe (1)

At least one oligonucleotide selected from:

Oligonucleotide that is at least one oligonucleotide having a sequence identical to that of a region extending from cytosine (C) at base 3518 to be considered as the first base to any one of the 15th to 19th bases in the direction toward the 5' end in SEQ ID NO: 1, with the cytosine being the 3' end, and Oligonucleotide that is at least one oligonucleotide having a sequence identical to that of a region extending from cytosine (C) at base 3517 to be considered as the first base to any one of the 14th to 19th bases in the direction toward the 5' end in SEQ ID NO: 1, with the cytosine being the 3' end.

Probe (2)

Oligonucleotide that is at least one oligonucleotide having a sequence identical to that of a region extending from cytosine (C) at base 3556 to be considered as the first base to any one of the 15th to 20th bases in the direction toward the 5' end in SEQ ID NO: 1, with the cytosine being the 3' end.

In the probe (1), base 3514 in SEQ ID NO: 1 is expressed with "r" and the "r" is A or G. In the probe (2), base 3543 in SEQ ID NO: 1 is expressed with "r" and the "r" is A or G.

Specific examples of Probe (1) and Probe (2) are indicated in the following table. "Tm(° C.)" indicated below in the table is Tm(° C.) obtained when each sequence indicated below in the table was hybridized with the sequence perfectly complementary thereto. The "Tm(° C.)" is a value calculated by using MELTCALC software (http://www.meltcalc.com/), with parameters including an oligonucleotide concentration of 0.2 µM and a sodium equivalent (Na eq.) of 50 mM.

TABLE 3

| Probe | Sequence | Tm(° C.) | SEQ. ID NO. |
|---|---|---|---|
| Probe (1) for SULT1A1*2 | 5'-ggagtttgtggggcGctcc-3' | 59.8 | 22 |
| | 5'-gagtttgtggggcActcc-3' | 54.3 | 23 |
| | 5'-agtttgtggggcActcc-3' | 53 | 24 |
| | 5'-gtttgtggggcActcc-3' | 51.3 | 25 |
| | 5'-tttgtggggcActcc-3' | 49.3 | 26 |
| | 5'-tggagtttgtggggcActc-3' | 56 | 43 |
| | 5'-ggagtttgtggggcActc-3' | 54.3 | 44 |
| | 5'-gagtttgtggggcActc-3' | 51.5 | 45 |
| | 5'-agtttgtggggcActc-3' | 50 | 46 |
| | 5'-gtttgtggggcActc-3' | 48.1 | 47 |
| | 5'-tttgtggggcActc-3' | 45.5 | 48 |
| Probe (2) for SULT1A1*3 | 5'-gacttcGtggttcagcacac-3' | 55.6 | 27 |
| | 5'-acttcGtggttcagcacac-3' | 54.6 | 28 |
| | 5'-cttcGtggttcagcacac-3' | 52.9 | 29 |
| | 5'-ttcGtggttcagcacac-3' | 51.6 | 30 |
| | 5'-tcGtggttcagcacac-3' | 50.7 | 31 |
| | 5'-cGtggttcagcacac-3' | 48.9 | 32 |

In probes (1) indicated in the above table, a probe that is expressed with SEQ ID NO: 22 is composed of a sequence identical to that of a region having G at base 3514 in SEQ ID NO: 1 and probes that are expressed with SEQ ID NOs: 23 to 26 and 43 to 48 are composed of a sequence identical to that of a region having A at base 3514 in SEQ ID NO: 1, and the capitalized base thereof indicates the base complementary to base 3514 in SEQ ID NO: 1. In each probe (1), the capitalized base can be expressed with "r", and the "r" may be either G or A. Each probe (2) indicated in the above table is composed of a sequence identical to that of a region having G at base 3543 in SEQ ID NO: 1, and the capitalized base indicates base 3543 in SEQ ID NO: 1. In each probe (2), the capitalized base can be expressed with "r", and the "r" may be either G or A. As described above, specific examples of the probe according to the present invention may be strands complementary to oligonucleotides indicated in the above table.

The aforementioned probes are examples and the present invention is not limited thereto. With respect to the probe for SULT1A1*2, a preferable probe is (P1') oligonucleotide consisting of the base sequence of SEQ ID NO: 23 or SEQ ID NO: 46. With respect to the probe for SULT1A1*3, a preferable probe is (P2') oligonucleotide consisting of the base sequence of SEQ ID NO: 30.

For example, when more than two types of probes are used as described above, it is preferable that they be labeled with different fluorescent dyes (fluorescent dyes that are detected at different wavelengths). For instance, when the probes indicated in the above table are guanine quenching probes, it is preferable that in each probe for SULT1A1*2 (P1 probe) and each probe for SULT1A1*3 (P2 probe), cytosine at the 3' end thereof be labeled with a fluorescent dye (for instance, BODIPY FL or TAMRA) as described above. Furthermore, a probe with the 5' end labeled with a fluorescent dye may have the 3' end, to which a phosphate group further may be added, in order to prevent the probe itself from elongating.

Next, with respect to the detection method of the present invention, a method of detecting two polymorphisms, SULT1A1*2 and SULT1A1*3, in the SULT1A1 gene using the following probes is described as an example. However, the present invention is not limited thereto.
<Probe>

```
Probe for SULT1A1*2              (SEQ ID NO: 23)
5'-gagtttgtggggcActcc-(BODIPY FL)-3',
or
                                 (SEQ ID NO: 46)
5'-agtttgtggggcActc-(BODIPY FL)-3'

Probe for SULT1A1*3              (SEQ ID NO: 30)
5'-ttcGtggttcagcacac-(TAMRA)-3'
```

First, using a reaction solution containing the aforementioned two labeled probes added thereto, PCR was performed as described above, and thereby the region of the SULT1A1 gene is amplified in the same reaction solution. The reaction solution contains, for example, a primer set for amplifying the SULT1A1 gene of the present invention, DNA polymerase, dNTP, a sample containing nucleic acid to serve as a template, and the aforementioned two probes. In addition to them, various additives that can be used for amplifying nucleic acid may be contained.

Next, the amplification products thus obtained are dissociated and then single-stranded DNA obtained through dissociation is hybridized with the labeled probes. This can be carried out through, for example, a change in the temperature of the reaction solution.

The heating temperature in the dissociation step is not particularly limited as long as it allows the amplification products to be dissociated. It is, for example, 85 to 95° C. The heating time also is not particularly limited and generally is 1 second to 10 minutes and preferably 1 second to 5 minutes.

The dissociated single-stranded DNA can be hybridized with the labeled probes by, for example, decreasing the heating temperature employed in the dissociation step after the dissociation step. The temperature condition is, for example, 40 to 50° C.

The temperature of the reaction solution is changed and thereby signal values that indicate the melting states of hybridization products between the amplification products and the labeled probes are measured. Specifically, for example, the reaction solution (the hybridization products between the single-stranded DNA and the labeled probes) is heated, and thereby the change in the signal values accompanying the temperature rise is measured. As described above, when, for example, a probe (guanine quenching probe), in which the base C at the end has been labeled, is used, fluorescence decreases (or quenches) in the state where the probe has been hybridized with the single-stranded DNA, while fluorescence is emitted in the state where the probe has been dissociated. Accordingly, for example, the hybridization product in which the fluorescence has decreased (or quenched) is heated gradually and the increase in fluorescence intensity accompanying the temperature rise may be measured.

The temperature range in which the change in fluorescence intensity is to be measured is not particularly limited. For example, the start temperature is room temperature to 85° C. and preferably 25 to 70° C., while the end temperature is, for example, 40 to 105° C. Furthermore, the rate of temperature rise is not particularly limited and is, for example, 0.1 to 20° C./sec and preferably 0.3 to 5° C./sec.

Next, the Tm value is determined by analyzing a change in the signal. Specifically, the amount of change in the fluorescence intensity per unit time at each temperature (−d fluorescence intensity increase/dt) is calculated from the fluorescence intensity obtained and the temperature at which the lowest value is obtained is determined as the Tm value. It is also possible to determine, as the Tm value, the point at which the amount of increase in the fluorescence intensity per unit time (fluorescence intensity increase/t) is the highest. On the contrary the amount of decrease in the fluorescence intensity is measured when the labeled probe used is not a quenching probe but a probe that does not exhibit a signal independently but exhibits a signal after hybridization.

In the present invention, in order to detect two polymorphisms, SULT1A1*2 and SULT1A1*3, the respective Tm values are determined under conditions according to each label of the two probes. BODIPY FL of a probe for SULT1A1*2, can be detected with, for example, a detection wavelength of 515 to 555 nm, and TAMRA of a probe for SULT1A1*3, can be detected with, for example, a detection wavelength of 585 to 700 nm. Further, when the label is Pacific Blue, it can be detected with, for example, a detection wavelength of 450 to 480 nm.

From such Tm values, the genotypes in the respective sites to be detected are determined. In the Tm analysis, the case of a perfectly complementary hybrid (match) results in a higher Tm value indicating dissociation than that obtained in the case of a hybrid including a different single base (mismatch). Accordingly, when with respect to the probe, the Tm value obtained in the case of a perfectly complementary hybrid and the Tm value obtained in the case of a hybrid including a different single base are determined beforehand, the genotype at each site to be detected can be determined. For example, in the case where the base located at the site to be detected is assumed to be of a mutation type (with, for instance, A at base 3514 in SEQ ID NO: 1), when using a probe complementary to the sequence to be detected containing the base, the polymorphism of the amplification product can be judged as a mutation type if the Tm value of the resultant hybrid is equal to the Tm value of a perfectly complementary hybrid. Furthermore, the polymorphism of the amplification product can be judged as a wildtype (with, for example, G at base 3514 in SEQ ID NO: 1) if the Tm value of the resultant hybrid is equal to the Tm value of the hybrid including a different single base (i.e. a lower value than the Tm value of the perfectly complementary hybrid). Moreover, when both of the Tm values are detected, it can be judged as heterozygote. Thus, the genotypes of the polymorphisms, SULT1A1*2 and SULT1A1*3, can be judged from the two Tm values with respect to the respective labeled probes.

In the present invention, for example, a change in the signal during hybridization may be measured instead of the method in which the temperature of a reaction solution containing the probes is increased (a hybridization product is heated) and a change in the signal accompanying the temperature rise is measured as described above. In other words, when the temperature of the reaction solution containing the aforementioned probes is decreased to form hybridization products, the change in the signal accompanying the temperature decrease may be measured.

Specifically, when using a labeled probe that exhibits a signal independently but does not exhibit a signal after hybridization (for example, a guanine quenching probe), the labeled probe emits fluorescence in the state where single-stranded DNA and the probe are dissociated, but the fluorescence decreases (or quenches) when a hybrid is formed through temperature decrease. Accordingly, for example, the temperature of the reaction solution is decreased gradually and the decrease in fluorescence intensity accompanying the temperature decrease may be measured. On the other hand, when using a labeled probe that does not exhibit a signal independently but exhibits a signal after hybridization, the labeled probe does not emit fluorescence in the state where single-stranded DNA and the probe are dissociated, but the fluorescence is emitted when a hybrid is formed through temperature decrease. Accordingly, for example, the temperature of the reaction solution is decreased gradually and thereby the increase in fluorescence intensity accompanying the temperature decrease may be measured.

When one of the two types of polymorphisms (SULT1A1*2 and SULT1A1*3) in the SULT1A1 gene are to be analyzed, for instance, one type of probe that hybridize to target sites to be detected may be used.

Next, examples of the present invention are described. However, the present invention is not limited by the following examples.

Example 1

Blood was collected from eight subjects using heparin lithium blood collection tubes (Samples 1 to 8). Subsequently, 10 μL of blood thus obtained and 90 μL of distilled water were mixed together. Further, 10 μL of this mixture and 90 μL of distilled water were mixed together. Thereafter, 10 μL of the mixture was added to 40 μL of PCR reaction solution having the following composition, and then PCR was performed using a thermal cycler. Conditions for PCR were as follows. That is, after treating at 95° C. for 60 seconds, one cycle of treatment at 95° C. for 1 second and at 66° C. for 10 seconds was repeated for 50 cycles, and further it was treated at 95° C. for 1 second and at 40° C. for 60 seconds. Subsequently, the PCR reaction solution was heated from 40° C. to 95° C. at a rate of temperature rise of 1° C./3 seconds, and the change in fluorescence intensity over time was measured. The measurement wavelength was 515 to 555 nm (for detection of the fluorescent dye, BODIPY FL) and 585 to 700 nm (for detection of the fluorescent dye, TAMRA). The time required for 50 cycles of PCR was approximately one hour.

TABLE 4

<PCR reaction solution; unit: μl>

| Distilled water | 23.225 |
|---|---|
| 5% NaN$_3$ | 0.4 |
| 20% BSA | 1 |
| 40% Glycerol | 3.125 |
| 10 × Gene Taq buffer* | 5 |
| 2.5 mM dNTPs | 4 |
| 100 mM MgCl$_2$ | 0.75 |
| 5 uM probe for SULT1A1*2 | 0.75 |
| 5 uM probe for SULT1A1*3 | 0.75 |
| 100 μM SULT1A1 F1 primer | 0.25 |
| 100 μM SULT1A1 R1 primer | 0.5 |
| 5 U/μl Gene Taq FP* | 0.25 |
| Total | 40 μL |

*Trade name, Gene Taq FP: manufactured by Nippon Gene Co., Ltd.

<Probes>

```
Probe for SULTL1A1*2            (SEQ ID NO: 23)
5'-gagtttgtggggcactcc-(BODIPY FL)-3'

Probe for SULT1A1*3             (SEQ ID NO: 30)
5'-ttcgtggttcagcacac-(TAMRA)-3'
```

<Primer Set>

```
SULT1A1 F1 primer               (SEQ ID NO: 7)
5'-tgaggttagagaaggggacccctttac-3'

SULT1A1 R1 primer               (SEQ ID NO: 18)
5'-gctgtggtccatgaactcctggg-3'
```

The Tm value of a hybrid that matches with the probe for SULT1A1*2 is 67.0° C. and that of a hybrid that mismatches therewith is 60.0° C. The Tm value of a hybrid that matches with the probe for SULT1A1*3 is 64.0° C. and that of a hybrid that mismatches therewith is 58.0° C.

Figure 2:
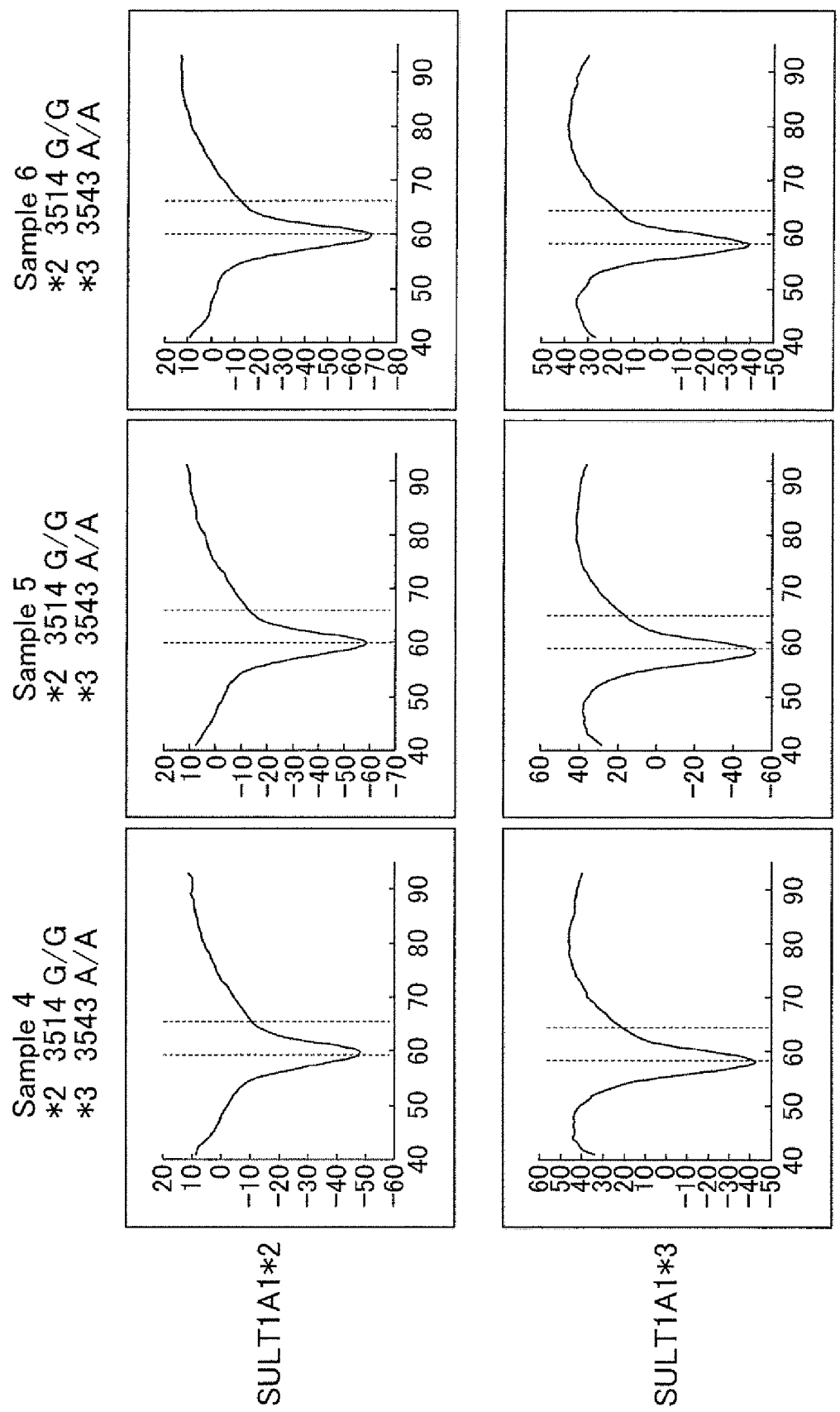
FIG. 2 shows graphs indicating the results of Tm analysis in Example 1 of the present invention described above.
Figure 3:
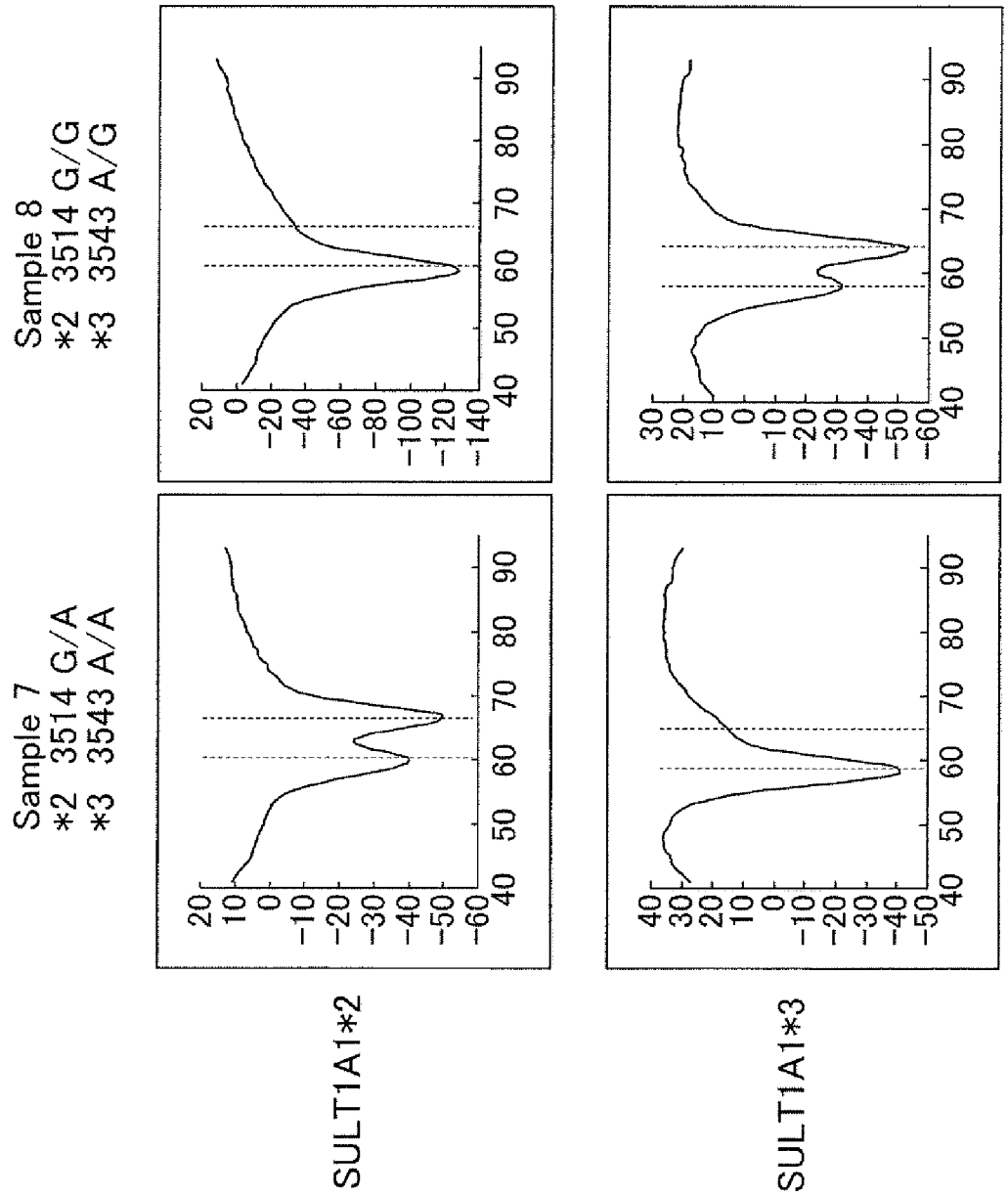
FIG. 3 shows graphs indicating the results of Tm analysis in Example 1 of the present invention described above.

Results of Samples 1 to 8 are indicated in FIGS. 1 to 3. These figures show graphs of Tm analysis that indicate the changes in fluorescence intensity accompanying temperature rise. The differential value of the vertical axis indicates "−d fluorescence intensity increase/dt", while the horizontal axis indicates temperature (the same applies below). As shown in these graphs, the genotype of SULT1A1*2 and SULT1A1*3 in each sample was determined from the peaks of the signals. In order to support the results of these examples, with respect to eight subjects, the genotype of SULT1A1*2 and SULT1A1*3 was confirmed by the RFLP method. As a result, the same results as those obtained in the example were obtained. Accordingly, the use of a primer set of the present invention made it possible to efficiently amplify the region including both of the sites to be detected of SULT1A1*2 and SULT1A1*3 in the SULT1A1 gene using a whole blood sample that had not been pretreated and to analyze two polymorphisms using the same reaction solution.

Example 2

Blood was collected from two subjects using EDTA blood collection tubes (Samples 1 and 2). Subsequently, 10 μL of blood thus obtained and 70 μL of diluent A described below were mixed together. Further, 10 μL of this mixture and 70 μL of diluent B described below were mixed together. Subsequently, 10 μL of the mixture thus obtained was heat-treated at 95° C. for five minutes. Thereafter, this was added to 46 μL of PCR reaction solution having the following composition, and then PCR was performed using a thermal cycler. Conditions for PCR were as follows. That is, after treating at 95° C. for 60 seconds, one cycle of treatment at 95° C. for 1 second and at 62° C. for 1.5 seconds was repeated for 50 cycles, and further it was treated at 95° C. for 1 second and at 40° C. for 60 seconds. Subsequently, the PCR reaction solution was heated from 40° C. to 75° C. at a rate of temperature rise of 1° C./3 seconds, and the change in fluorescence intensity over time was measured. The measurement wavelength was 515 to 555 nm (for detection of the fluorescent dye, BODIPY FL).

<Diluent A>
10 mM Tris-HCl (pH 8), 0.1 mM EDTA, 0.05% Na$_3$, 0.3% SDS

<Diluent B>
10 mM Tris-HCl (pH 8), 0.1 mM EDTA, 0.05% NaN$_3$

TABLE 5

<PCR reaction solution; unit: μl>

| Distilled water | 22.5 |
|---|---|
| 5% NaN$_3$ | 0.5 |
| 20% BSA | 0.5 |
| 40% Glycerol | 10 |
| 10 × Gene Taq buffer* | 5 |
| 2.5 mM dNTPs | 4 |

TABLE 5-continued

<PCR reaction solution; unit: μl>

| | |
|---|---|
| 100 mM MgCl$_2$ | 0.5 |
| 5 uM probe for SULT1A1*2 | 2 |
| 100 μM SULT1A1 F1 primer | 0.25 |
| 100 μM SULT1A1 R1 primer | 0.5 |
| 5 U/μl Gene Taq FP* | 0.25 |
| Total | 46 μL |

*Trade name, Gene Taq FP: manufactured by Nippon Gene Co., Ltd.

<Probe>

```
Probe for SULT1A1*2           (SEQ ID NO: 46)
5'-agtttgtggggcActc-(BODIPY FL)-3'
```

<Primer Set>

```
SULT1A1 F1 primer              (SEQ ID NO: 7)
5'-tgaggttagagaaggggaccccttttac-3'

SULT1A1 R1 primer             (SEQ ID NO: 39)
5'-ggtggtgtagttggtcatagggttctt-3'
```

The Tm value of a hybrid that matches with the probe for SULT1A1*2 is 59° C. and that of a hybrid that, mismatches therewith is 51° C.

Figure 4:
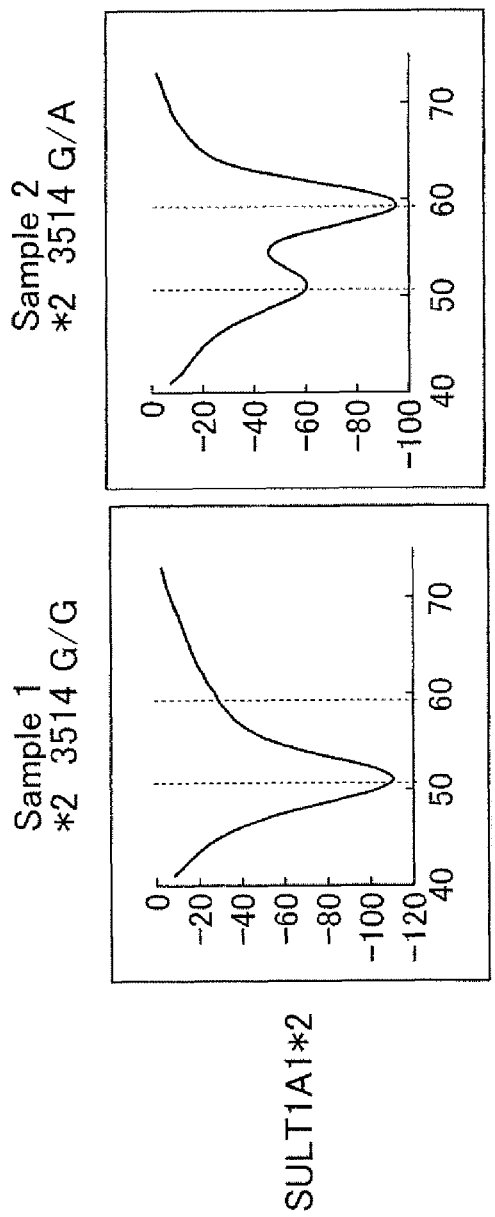
FIG. 4 shows graphs indicating the results of Tm analysis in Example 2 of the present invention.

Results of Samples 1 and 2 are indicated in FIG. 4. FIG. 4 shows graphs of Tm analysis that indicate the changes in fluorescence intensity accompanying temperature rise. The differential value of the vertical axis indicates "−d fluorescence intensity increase/dt", while the horizontal axis indicates temperature. As shown in these graphs, the genotype of SULT1A1*2 in the samples 1 and 2 was determined from the peaks of the signals. In order to support the results of this example, with respect to two subjects, the genotype of SULT1A1*2 was confirmed by the RFLP method. As a result, the same results as those obtained in the example were obtained. Accordingly, the use of a primer set of the present invention made it possible to efficiently amplify the region including both of the sites to be detected of SULT1A1*2 in the SULT1A1 gene using a whole blood sample that had not been pretreated and to analyze two polymorphisms using the same reaction solution.

INDUSTRIAL APPLICABILITY

As described above, the primer set of the present invention makes it possible to specifically and efficiently amplify a region including both sites where polymorphisms, SULT1A1*2 and SULT1A1*3, are generated in the SULT1A1 gene. This allows time and cost to be reduced, which is different from the conventional methods as described above. Furthermore, as described above, since the region including the both sites to be detected of two polymorphisms are amplified specifically, for example, the use of two types of probes complementary to a sequence to be detected including each site to be detected makes it possible to perform Tm analysis directly using the aforementioned reaction solution to type the two polymorphisms. Moreover, since amplification and typing can be carried out using one reaction solution, the operation can be automated. The use of the primer set of the present invention allows a pretreatment to be omitted even in the case of, for example, a contaminated sample (for instance, whole blood or oral mucosa), and therefore the amplification reaction can be carried out quicker and more easily. Furthermore, when the primer set of the present invention is used, the amplification reaction can be carried out with higher amplification efficiency as compared to conventional cases and thus the reaction time can also be shortened. According to the primer set of the present invention, the reagent including the same, as well as the method of manufacturing an amplification product using them, since the polymorphism in the SULT1A1 gene can be analyzed quickly and simply, it can be said that they are considerably effective in the field of medicine.

[Sequence Table] TF07042-01.ST25.txt

The invention claimed is:

1. A probe consisting of SEQ ID NO: 30.

2. The probe according to claim 1, wherein the probe is a fluorescently labeled probe.

3. A reagent composition comprising the probe according to claim 1.

4. The reagent composition according to claim 3, wherein the probe is a fluorescently labeled probe.

5. The reagent composition according to claim 3, further comprising primer set (1), wherein the primer set (1) is a primer set of a pair of primers including a forward primer comprising oligonucleotide (F1) and a reverse primer comprising oligonucleotide (R1), wherein the oligonucleotide (F1) consists of a sequence identical to that of a region extending from cytosine (C) at base 3418 to be considered as the first base to any one of the $24^{th}$ to $33^{rd}$ bases in the direction toward the 5' end in the base sequence of SEQ ID NO: 1, with the cytosine (C) being the 3' end, and the oligonucleotide (R1) consists of an oligonucleotide selected from the group consisting of:

an oligonucleotide complementary to a region extending from cytosine (C) at base 3607 to be considered as the first base to any one of the $20^{th}$ to $29^{th}$ bases in the direction toward the 3' end in the base sequence of SEQ ID NO: 1, with guanine (G) complementary to the cytosine (C) at base 3607 being the 3' end, and an oligonucleotide complementary to a region extending from adenine (A) at base 3576 to be considered as the first base to any one of the $24^{th}$ to $33^{rd}$ bases in the direction toward the 3' end in the base sequence of SEQ ID NO: 1, with thymine (T) complementary to the adenine (A) at base 3576 being the 3' end.

6. A polymorphism analysis method of analyzing a polymorphism of a site to be detected in the SULT1A1 gene, wherein the method comprises the following processes (i) to (iv):

(i) amplifying a region including base 3543 in SEQ ID NO: 1 as a site to be detected in the SULT1A1 gene in a reaction solution with nucleic acid contained in a sample being used as a template, (ii) preparing a reaction solution that contains the amplification product obtained in the process (i) and the probe according to claim 1, (iii) measuring signal values that indicate molten states of a hybridization product between the amplification product and the probe while changing the temperature of the reaction solution, and (iv) determining a polymorphism of the site to be detected from a change in the signal values accompanying a change in the temperature.

7. The polymorphism analysis method according to claim 6, wherein, in the process (i), the probe is added to the reaction solution prior to an amplification reaction.

8. The polymorphism analysis method according to claim 6, wherein the sample is a biological sample.

9. The polymorphism analysis method according to claim 8, wherein the biological sample is whole blood.

10. The polymorphism analysis method according to claim 6, wherein, in the process (i), the amplification of the SULT1A1 gene is carried out in the reaction solution using primer set (1), wherein the primer set (1) is a primer set of a pair of primers including a forward primer comprising oligonucleotide (F1) and a reverse primer comprising oligonucleotide (R1), wherein the oligonucleotide (F1) consists of a sequence identical to that of a region extending from cytosine (C) at base 3418 to be considered as the first base to any one of the 24$^{th}$ to 33$^{rd}$ bases in the direction toward the 5' end in the base sequence of SEQ ID NO: 1, with the cytosine (C) being the 3' end, and the oligonucleotide (R1) is an oligonucleotide selected from the group consisting of:

an oligonucleotide complementary to a region extending from cytosine (C) at base 3607 to be considered as the first base to any one of the 20$^{th}$ to 29$^{th}$ bases in the direction toward the 3' end in the base sequence of SEQ ID NO: 1, with guanine (G) complementary to the cytosine (C) at base 3607 being the 3' end, and an oligonucleotide complementary to a region extending from adenine (A) at base 3576 to be considered as the first base to any one of the 24$^{th}$ to 33$^{rd}$ bases in the direction toward the 3' end in the base sequence of SEQ ID NO: 1, with thymine (T) complementary to the adenine (A) at base 3576 being the 3' end.

* * * * *

SEQUENCE LISTING

```
<160> NUMBER OF SEQ ID NOS: 48

<210> SEQ ID NO 1
<211> LENGTH: 4030
<212> TYPE: DNA
<213> ORGANISM: Homo sapiens

<400> SEQUENCE: 1
ggatcctggc cactgcagcc ttgaattcct gggctcaagt gattctcttg cctcagcctc      60
tggagtagct aggactacag gccctcatca tcctgcctgg ttaatgttta agaatttttt     120
taaagatttt tagagatggg gtcttgcaat gctgcaccag gttggtctcc aactcctggc     180
ctcagcctcc ctagggtctg ggattatagg tgggagccac cctgcctagg cctgtgcttt     240
tgctgagtca tcagagtttt gttcattccc acagcagctc tggcccctag tagcagctca     300
gttcctcaat gggccgtgtt tgtcctggag cccagatgga ctgtggccag gcaagtggat     360
cacagcctgg ctggcctggg cggtttccac atgtgagggg ctgaggggct caaggagggg     420
agcatctcca ctgggtggag gctgggggtc ccagcaggaa atggtgagac aaaggcgct     480 ggctggcagg gagacagcac aggaaggtcc tagagcttcc tcagtgcagc tggactctcc     540
tggagacctt cacacacct gatatctggg ccttgcccga cgagggtgct ttcactggtc      600
```

```
tgcaccatgg cccaggccct gggattttga acagctccgc aggtgaatga aaggtgaggc    660
caggctgggg aaccaccgca ttagagcccg acctggtttt cagccccagc cccgccactg    720
actggctttg tgagtgcggg caagtcactc agcctcccta ggcctcagtg acttccctga    780
aagcaagaat tccactttct tgctgttgtg atggtggtaa gggaacgggc ctggctctgg    840
ccctgacgca ggaacatgga gctgatccag gacacctccc gcccgccact ggagtacgtg    900
aaggggggtcc cgctcatcaa gtactttgca gaggcactgg ggcccctgca gagcttccag    960
gcccggcctg atgacctgct catcagcacc taccccaagt ccggtaagtg aggagggcca   1020
cccaccctct cccaggtggc agtccccacc ttggccagcg aggtcgtgcc ctcagcctgc   1080
tcacctccca tctccctccc tctccaggca ccacctgggt gagccagatt ctggacatga   1140
tctaccaggg tggtgacctg gagaagtgtc accgagctcc catcttcatg cgggtgccct   1200
tccttgagtt caaagcccca gggattccct caggtgtgtg agtgtgtcct gggtgcaagg   1260
ggagtggagg aagacagggc tggggcttca gctcaccaga ccttccctga cccactgctc   1320
agggatggag actctgaaag acacaccggc cccacgactc ctgaagacac acctgcccct   1380
ggctctgctc ccccagactc tgttggatca gaaggtcaag gtgaggcagg gcacagtgtt   1440
tcacatccat aatcccagca ctttgggagg ctgaggcagg cagatcacct gaggttggga   1500
gtttgagagc ccctgagca acatagaaga accttgtctc tactaaaaat acaaaattag   1560
ccgggtgtgg tggcgggtgc ctgtaatccc agctactccg aagcctgaga caggagaatc   1620
acttgaaccc gggagaagga ggttgtggtg agccagagat cccaccattg cattccagcc   1680
tgagcaacaa gagcaaaact cacaaaaata aataaataaa taaatatata aataaaaata   1740
aaactgtggc acctgtggtg gctcactgct gtaatgccag cactttggga ggccaaattg   1800
ggtggatcac ttgagctcag gagttacaga ccagcccggg aaacatgggg aacttccatc   1860
tctataaaaa tgcaaaatat cagcaggggca tggtggcatg cgcgctgtagt tccagctact   1920
ggaaagtctg aggttggagg attgcttgag cctgggaggt caaggttgca gtgagttatt   1980
atcactccag tgcactccaa cttgggcgac agaaaaaaag aaagaccaag gtctttttc    2040
ttttttgaga ttgtctcaat aaataaataa atgaataaat aaaaataaaa taaagtaaaa   2100
taaatcccac aattaaaaga aaaagcaaag gtccaggtgt ggggcatgtg aatccaggga   2160
aggaggccct ggctcagccc agctttggtc ctgttcttct gggaaagtcg cctcacttcc   2220
tccagccttg tctcatcttc tgcggcgggg actgtctgcc tcttgctctg atgaccaaga   2280
acgtaagact cttcagtgta gacctaagaa agctagaggg tgggtcctca caggcccaca   2340
aaatttggtg gcggtgggat cacggctggt ggagcatgcc ttgctccaga tcggggtgtg   2400
acgcattgat gcagattata ttactataga atatgatggt ctcagggacc aggcaggact   2460
ttggcttctg agcagggttc agatcctgac ttggccctac cggtgccgtg agatctcaaa   2520
caagtcagcc tctaagcctc aggttcctcc tttgccaatc aagagatga gctggcctgg    2580
ggcaggctgt gtggtgatgg tgctgggggtt gagtcttctg ccctgcagg tggtctatgt    2640
tgcccgcaac gcaaaggatg tggcagtttc ctactaccac ttctaccaca tggccaaggt   2700
gcaccctgag cctgggacct gggacagctt cctggagaag ttcatggtcg gagaaggtgg   2760
gtttgatggg aggaaggaaa gtgtggagcc gaggggtggt ggctacaacg cacagcaacc   2820
ctgtgttggc accccttgcc tgcttctcca gtgtcctacg gatcctggta ccagcacgtg   2880
caggagtggt gggagctgag ccgcacccac cctgttctct acctcttcta tgaagacatg   2940
aaggaggtga gaccacctgt gaagcttccc tccatgtgac acctgggggc cggcacctca   3000
```

```
cagggaccca ccaaggtcac ccagccccct cccttggcag cccccacagc aggcccggat    3060
tccccatcct gccttcttgg cccaggcctc cccgctacag gccccacctg gcagcgggcc    3120
ccacacagct ctcatctccc acatctgagt cagctgcatg gggggccacg gatcagaaac    3180
ttagtcctat tgctactccc tgccaaaggg tgtgccaccc agggccacag tcatggaaga    3240
agaccatcac ggtcctcacc cataggagcc aagcccagct catgatggga tcacagggca    3300
gacagcaatt ctttttaccc ccgggactgg ggccctgggg ttgaggagtt ggctctgcag    3360
ggtttctagg agaagtggcc agatcgcctc tgaggttaga gaaggggacc ccttttactt    3420
ttcctgaatc agcaatccga gcctccactg aggagccctc tgctgctcag aaccccaaaa    3480
gggagattca aaagatcctg gagtttgtgg ggcactccct gccagaggag accgtggact    3540
tcatggttca gcacacgtcg ttcaaggaga tgaagaagaa ccctatgacc aactacacca    3600
ccgtccccca ggagttcatg gaccacagca tctccccctt catgaggaaa ggtgggtgct    3660
ggccagtacg ggggtttggg gcgggtggga gcagcagctg cagcctcccc ataggcactc    3720
ggggcctccc ctgggatgag actccagctt tgctccctgc cttcctcccc caggcatggc    3780
tggggactgg aagaccacct tcaccgtggc gcagaatgag cgcttcgatg cggactatgc    3840
ggagaagatg gcaggctgca gcctcagctt ccgctctgag ctgtgagagg ggctcctggg    3900
gtcactgcag agggagtgtg cgaatcaaac ctgaccaagc ggctcaagaa taaaatgatga    3960 attgagggcc tgggacggta ggtcatgtct gtaatcccag caatttggag gctgaggtgg    4020
gaggatcata                                                          4030

<210> SEQ ID NO 2
<211> LENGTH: 33
<212> TYPE: DNA
<213> ORGANISM: Artificial
<220> FEATURE:
<223> OTHER INFORMATION: forward primer

<400> SEQUENCE: 2
gcctctgagg ttagagaagg ggaccccttt tac                                 33

<210> SEQ ID NO 3
<211> LENGTH: 32
<212> TYPE: DNA
<213> ORGANISM: Artificial
<220> FEATURE:
<223> OTHER INFORMATION: forward primer

<400> SEQUENCE: 3
cctctgaggt tagagaaggg gaccccttttt ac                                 32

<210> SEQ ID NO 4
<211> LENGTH: 31
<212> TYPE: DNA
<213> ORGANISM: Artificial
<220> FEATURE:
<223> OTHER INFORMATION: forward primer

<400> SEQUENCE: 4
ctctgaggtt agagaagggg accccttttta c                                  31

<210> SEQ ID NO 5
<211> LENGTH: 30
<212> TYPE: DNA
<213> ORGANISM: Artificial
<220> FEATURE:
<223> OTHER INFORMATION: forward primer
```

<400> SEQUENCE: 5
tctgaggtta gagaagggga cccctttac                                    30

<210> SEQ ID NO 6
<211> LENGTH: 29
<212> TYPE: DNA
<213> ORGANISM: Artificial
<220> FEATURE:
<223> OTHER INFORMATION: forward primer

<400> SEQUENCE: 6
ctgaggttag agaagggac ccctttac                                       29

<210> SEQ ID NO 7
<211> LENGTH: 28
<212> TYPE: DNA
<213> ORGANISM: Artificial
<220> FEATURE:
<223> OTHER INFORMATION: forward primer

<400> SEQUENCE: 7
tgaggttaga gaaggggacc ccttttac                                       28

<210> SEQ ID NO 8
<211> LENGTH: 27
<212> TYPE: DNA
<213> ORGANISM: Artificial
<220> FEATURE:
<223> OTHER INFORMATION: forward primer

<400> SEQUENCE: 8
gaggttagag aaggggaccc cttttac                                         27

<210> SEQ ID NO 9
<211> LENGTH: 26
<212> TYPE: DNA
<213> ORGANISM: Artificial
<220> FEATURE:
<223> OTHER INFORMATION: forward primer

<400> SEQUENCE: 9
aggttagaga aggggacccc ttttac                                           26

<210> SEQ ID NO 10
<211> LENGTH: 25
<212> TYPE: DNA
<213> ORGANISM: Artificial
<220> FEATURE:
<223> OTHER INFORMATION: forward primer

<400> SEQUENCE: 10
ggttagagaa ggggaccccct tttac                                             25

<210> SEQ ID NO 11
<211> LENGTH: 24
<212> TYPE: DNA
<213> ORGANISM: Artificial
<220> FEATURE:
<223> OTHER INFORMATION: forward primer

<400> SEQUENCE: 11
gttagagaag gggacccctt ttac                                                24

<210> SEQ ID NO 12
<211> LENGTH: 29

```
<212> TYPE: DNA
<213> ORGANISM: Artificial
<220> FEATURE:
<223> OTHER INFORMATION: reverse primer

<400> SEQUENCE: 12
ggagatgctg tggtccatga actcctggg                                            29

<210> SEQ ID NO 13
<211> LENGTH: 28
<212> TYPE: DNA
<213> ORGANISM: Artificial
<220> FEATURE:
<223> OTHER INFORMATION: reverse primer

<400> SEQUENCE: 13
gagatgctgt ggtccatgaa ctcctggg                                             28

<210> SEQ ID NO 14
<211> LENGTH: 27
<212> TYPE: DNA
<213> ORGANISM: Artificial
<220> FEATURE:
<223> OTHER INFORMATION: reverse primer

<400> SEQUENCE: 14
agatgctgtg gtccatgaac tcctggg                                              27

<210> SEQ ID NO 15
<211> LENGTH: 26
<212> TYPE: DNA
<213> ORGANISM: Artificial
<220> FEATURE:
<223> OTHER INFORMATION: reverse primer

<400> SEQUENCE: 15
gatgctgtgg tccatgaact cctggg                                               26

<210> SEQ ID NO 16
<211> LENGTH: 25
<212> TYPE: DNA
<213> ORGANISM: Artificial
<220> FEATURE:
<223> OTHER INFORMATION: reverse primer

<400> SEQUENCE: 16
atgctgtggt ccatgaactc ctggg                                                25

<210> SEQ ID NO 17
<211> LENGTH: 24
<212> TYPE: DNA
<213> ORGANISM: Artificial
<220> FEATURE:
<223> OTHER INFORMATION: reverse primer

<400> SEQUENCE: 17
tgctgtggtc catgaactcc tggg                                                 24

<210> SEQ ID NO 18
<211> LENGTH: 23
<212> TYPE: DNA
<213> ORGANISM: Artificial
<220> FEATURE:
<223> OTHER INFORMATION: reverse primer

<400> SEQUENCE: 18
gctgtggtcc atgaactcct ggg                                                  23
```

<210> SEQ ID NO 19
<211> LENGTH: 22
<212> TYPE: DNA
<213> ORGANISM: Artificial
<220> FEATURE:
<223> OTHER INFORMATION: reverse primer

<400> SEQUENCE: 19
ctgtggtcca tgaactcctg gg                                    22

<210> SEQ ID NO 20
<211> LENGTH: 21
<212> TYPE: DNA
<213> ORGANISM: Artificial
<220> FEATURE:
<223> OTHER INFORMATION: reverse primer

<400> SEQUENCE: 20
tgtggtccat gaactcctgg g                                     21

<210> SEQ ID NO 21
<211> LENGTH: 20
<212> TYPE: DNA
<213> ORGANISM: Artificial
<220> FEATURE:
<223> OTHER INFORMATION: reverse primer

<400> SEQUENCE: 21
gtggtccatg aactcctggg                                       20

<210> SEQ ID NO 22
<211> LENGTH: 19
<212> TYPE: DNA
<213> ORGANISM: Artificial
<220> FEATURE:
<223> OTHER INFORMATION: probe

<400> SEQUENCE: 22
ggagtttgtg gggcgctcc                                        19

<210> SEQ ID NO 23
<211> LENGTH: 18
<212> TYPE: DNA
<213> ORGANISM: Artificial
<220> FEATURE:
<223> OTHER INFORMATION: probe

<400> SEQUENCE: 23
gagtttgtgg ggcactcc                                         18

<210> SEQ ID NO 24
<211> LENGTH: 17
<212> TYPE: DNA
<213> ORGANISM: Artificial
<220> FEATURE:
<223> OTHER INFORMATION: probe

<400> SEQUENCE: 24
agtttgtggg gcactcc                                          17

<210> SEQ ID NO 25
<211> LENGTH: 16
<212> TYPE: DNA
<213> ORGANISM: Artificial
<220> FEATURE:
<223> OTHER INFORMATION: probe

```
<400> SEQUENCE: 25
gtttgtgggg cactcc                                                   16

<210> SEQ ID NO 26
<211> LENGTH: 15
<212> TYPE: DNA
<213> ORGANISM: Artificial
<220> FEATURE:
<223> OTHER INFORMATION: probe

<400> SEQUENCE: 26
tttgtggggc actcc                                                    15

<210> SEQ ID NO 27
<211> LENGTH: 20
<212> TYPE: DNA
<213> ORGANISM: Artificial
<220> FEATURE:
<223> OTHER INFORMATION: probe

<400> SEQUENCE: 27
gacttcgtgg ttcagcacac                                               20

<210> SEQ ID NO 28
<211> LENGTH: 19
<212> TYPE: DNA
<213> ORGANISM: Artificial
<220> FEATURE:
<223> OTHER INFORMATION: probe

<400> SEQUENCE: 28
acttcgtggt tcagcacac                                                19

<210> SEQ ID NO 29
<211> LENGTH: 18
<212> TYPE: DNA
<213> ORGANISM: Artificial
<220> FEATURE:
<223> OTHER INFORMATION: probe

<400> SEQUENCE: 29
cttcgtggtt cagcacac                                                 18

<210> SEQ ID NO 30
<211> LENGTH: 17
<212> TYPE: DNA
<213> ORGANISM: Artificial
<220> FEATURE:
<223> OTHER INFORMATION: probe

<400> SEQUENCE: 30
ttcgtggttc agcacac                                                  17

<210> SEQ ID NO 31
<211> LENGTH: 16
<212> TYPE: DNA
<213> ORGANISM: Artificial
<220> FEATURE:
<223> OTHER INFORMATION: probe

<400> SEQUENCE: 31
tcgtggttca gcacac                                                   16

<210> SEQ ID NO 32
<211> LENGTH: 15
```

```
<212> TYPE: DNA
<213> ORGANISM: Artificial
<220> FEATURE:
<223> OTHER INFORMATION: probe

<400> SEQUENCE: 32
cgtggttcag cacac                                                    15

<210> SEQ ID NO 33
<211> LENGTH: 33
<212> TYPE: DNA
<213> ORGANISM: Artificial
<220> FEATURE:
<223> OTHER INFORMATION: reverse primer

<400> SEQUENCE: 33
ggggacggtg gtgtagttgg tcatagggtt ctt                                33

<210> SEQ ID NO 34
<211> LENGTH: 32
<212> TYPE: DNA
<213> ORGANISM: Artificial
<220> FEATURE:
<223> OTHER INFORMATION: reverse primer

<400> SEQUENCE: 34
gggacggtgg tgtagttggt catagggttc tt                                 32

<210> SEQ ID NO 35
<211> LENGTH: 31
<212> TYPE: DNA
<213> ORGANISM: Artificial
<220> FEATURE:
<223> OTHER INFORMATION: reverse primer

<400> SEQUENCE: 35
ggacggtggt gtagttggtc atagggttct t                                  31

<210> SEQ ID NO 36
<211> LENGTH: 30
<212> TYPE: DNA
<213> ORGANISM: Artificial
<220> FEATURE:
<223> OTHER INFORMATION: reverse primer

<400> SEQUENCE: 36
gacggtggtg tagttggtca tagggttctt                                    30

<210> SEQ ID NO 37
<211> LENGTH: 29
<212> TYPE: DNA
<213> ORGANISM: Artificial
<220> FEATURE:
<223> OTHER INFORMATION: reverse primer

<400> SEQUENCE: 37
acggtggtgt agttggtcat agggttctt                                     29

<210> SEQ ID NO 38
<211> LENGTH: 28
<212> TYPE: DNA
<213> ORGANISM: Artificial
<220> FEATURE:
<223> OTHER INFORMATION: reverse primer

<400> SEQUENCE: 38
cggtggtgta gttggtcata gggttctt                                      28
```

```
<210> SEQ ID NO 39
<211> LENGTH: 27
<212> TYPE: DNA
<213> ORGANISM: Artificial
<220> FEATURE:
<223> OTHER INFORMATION: reverse primer

<400> SEQUENCE: 39
ggtggtgtag ttggtcatag ggttctt                                        27

<210> SEQ ID NO 40
<211> LENGTH: 26
<212> TYPE: DNA
<213> ORGANISM: Artificial
<220> FEATURE:
<223> OTHER INFORMATION: reverse primer

<400> SEQUENCE: 40
gtggtgtagt tggtcatagg gttctt                                         26

<210> SEQ ID NO 41
<211> LENGTH: 25
<212> TYPE: DNA
<213> ORGANISM: Artificial
<220> FEATURE:
<223> OTHER INFORMATION: reverse primer

<400> SEQUENCE: 41
tggtgtagtt ggtcataggg ttctt                                          25

<210> SEQ ID NO 42
<211> LENGTH: 24
<212> TYPE: DNA
<213> ORGANISM: Artificial
<220> FEATURE:
<223> OTHER INFORMATION: reverse primer

<400> SEQUENCE: 42
ggtgtagttg gtcatagggt tctt                                           24

<210> SEQ ID NO 43
<211> LENGTH: 19
<212> TYPE: DNA
<213> ORGANISM: Artificial
<220> FEATURE:
<223> OTHER INFORMATION: probe

<400> SEQUENCE: 43
tggagtttgt ggggcactc                                                 19

<210> SEQ ID NO 44
<211> LENGTH: 18
<212> TYPE: DNA
<213> ORGANISM: Artificial
<220> FEATURE:
<223> OTHER INFORMATION: probe

<400> SEQUENCE: 44
ggagtttgtg gggcactc                                                  18

<210> SEQ ID NO 45
<211> LENGTH: 17
<212> TYPE: DNA
<213> ORGANISM: Artificial
<220> FEATURE:
<223> OTHER INFORMATION: probe
```

```
<400> SEQUENCE: 45
gagtttgtgg ggcactc                                              17

<210> SEQ ID NO 46
<211> LENGTH: 16
<212> TYPE: DNA
<213> ORGANISM: Artificial
<220> FEATURE:
<223> OTHER INFORMATION: probe

<400> SEQUENCE: 46
agtttgtggg gcactc                                               16

<210> SEQ ID NO 47
<211> LENGTH: 15
<212> TYPE: DNA
<213> ORGANISM: Artificial
<220> FEATURE:
<223> OTHER INFORMATION: probe

<400> SEQUENCE: 47
gtttgtgggg cactc                                                15

<210> SEQ ID NO 48
<211> LENGTH: 14
<212> TYPE: DNA
<213> ORGANISM: Artificial
<220> FEATURE:
<223> OTHER INFORMATION: probe

<400> SEQUENCE: 48
tttgtggggc actc                                                 14
```